United States Patent
Kim et al.

(10) Patent No.: US 10,258,674 B2
(45) Date of Patent: Apr. 16, 2019

(54) NANOPARTICLES COMPRISING AMINOACYL TRNA SYNTHETASE AND ANTICANCER COMPOSITION COMPRISING SAME

(71) Applicant: Medicinal Bioconvergence Research Center, Gyeonggi-do (KR)

(72) Inventors: Sunghoon Kim, Seoul (KR); Min Chul Park, Gyeonggi-do (KR)

(73) Assignee: MEDICINAL BIOCONVERGENCE RESEARCH CENTER, Gyeonggi-Do (KR)

(*) Notice: Subject to any disclaimer, the term of this patent is extended or adjusted under 35 U.S.C. 154(b) by 152 days.

(21) Appl. No.: 15/362,196

(22) Filed: Nov. 28, 2016

(65) Prior Publication Data

US 2017/0072031 A1    Mar. 16, 2017

Related U.S. Application Data

(63) Continuation of application No. PCT/KR2015/005370, filed on May 28, 2015.

(30) Foreign Application Priority Data

May 28, 2014  (KR) .................. 10-2014-0064762

(51) Int. Cl.

| | | |
|---|---|---|
| *C12N 9/00* | (2006.01) | |
| *A61K 38/53* | (2006.01) | |
| *A61K 38/43* | (2006.01) | |
| *C12P 21/00* | (2006.01) | |
| *A61K 38/17* | (2006.01) | |

(52) U.S. Cl.
CPC .......... *A61K 38/53* (2013.01); *A61K 38/1709* (2013.01); *A61K 38/179* (2013.01); *A61K 38/43* (2013.01); *C12N 9/00* (2013.01); *C12N 9/93* (2013.01); *C12P 21/00* (2013.01); *C12Y 601/01004* (2013.01); *C12Y 601/01005* (2013.01); *C12Y 601/01014* (2013.01)

(58) Field of Classification Search
CPC .. A61K 38/1709; A61K 38/179; A61K 38/43; A61K 38/53; C12N 9/00; C12N 9/93; C12P 21/00; C12Y 601/01004; C12Y 601/01005; C12Y 601/01014
USPC ...... 435/183, 375; 424/94.5, 94.3, 93.7, 450
See application file for complete search history.

(56) References Cited

U.S. PATENT DOCUMENTS

| | | |
|---|---|---|
| 2013/0129703 A1 | 5/2013 | Chiang et al. |
| 2013/0209434 A1 | 8/2013 | Greene et al. |

FOREIGN PATENT DOCUMENTS

| | | |
|---|---|---|
| KR | 20100040697 A | 4/2010 |
| KR | 1011024850000 B1 | 1/2012 |

OTHER PUBLICATIONS

Rocks et al. Science 307 (5716), 1746-1752. (Year: 2005).*
Kim, Sunghoon et al., Aminoacyl-tRNA synthetases and tumorigenesis: more than housekeeping, Nature Reviews Cancer, Oct. 2011, pp. 708-718, vol. 11, Macmillan Publishers Limited, United Kingdom.
Park, Sang Gyu et al., Aminoacyl tRNA synthetases and their connections to disease, Proceedings of the National Academy of Sciences of the United States of America, Aug. 12, 2008, pp. 11043-11049, vol. 105, No. 32, The National Academy of Sciences of the USA, Washington DC.
Jung, Hyun Suk et al., Head-Head and Head-Tail Interaction: A General Mechanism for Switching Off Myosin II Activity in Cells, Molecular Biology of the Cell, Aug. 2008, pp. 3234-3242, vol. 19, The American Society for Cell Biology, Bethesda, Maryland.

* cited by examiner

*Primary Examiner* — Janet L Epps-Smith
(74) *Attorney, Agent, or Firm* — Levenfeld Pearlstein, LLC

(57) ABSTRACT

The present invention relates to nanoparticles comprising aminoacyl tRNA synthetase and an anticancer composition comprising the same and, specifically, to nanoparticles which comprise glycyl-tRNA synthetase (GRS), leucyl-tRNA synthetase (LRS), and isoleucyl-tRNA synthetase (IRS), and have anticancer or immunostimulating activity; a pharmaceutical composition for preventing or treating cancer, comprising the nanoparticles as an active ingredient; a composition for immunostimulation; and a method for preparing the nanoparticles.

11 Claims, 30 Drawing Sheets

Specification includes a Sequence Listing.

Fig. 3b

| Exosome SNAP | |
|---|---|
| ALB | - |
| ANXA2 | - |
| CD63 | - |
| CD81 | - |
| CD9 | - |
| PDCD6IP | - |
| SDCBP | - |
| YWHAE | - |
| YWHAZ | - |

Fig. 12b
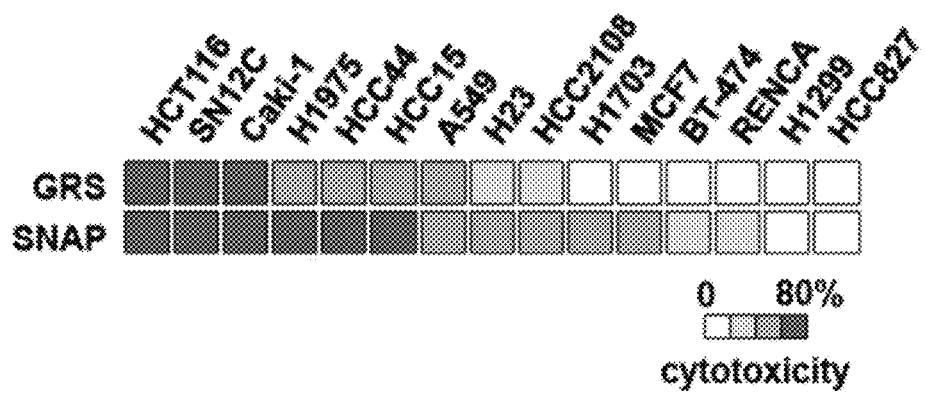
Fig. 13a
| tumor volume > 100 mm³ | | |
|---|---|---|
| con | GRS | SNAP |
| 6/6 | 2/6 | 2/6 |
Fig. 13b
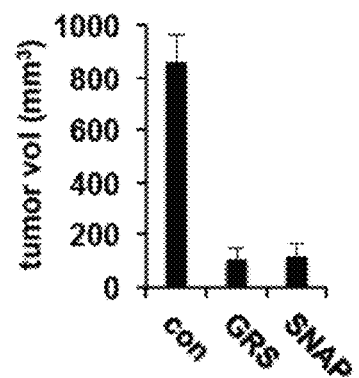

NANOPARTICLES COMPRISING AMINOACYL TRNA SYNTHETASE AND ANTICANCER COMPOSITION COMPRISING SAME

This is a Continuation of PCT Application No. PCT/KR2015/005370, filed May 26, 2015, which claims the benefit of Korean Application No. 10-2014-0064762 filed or 28 May 2014, the contents of which axe incorporated fully by reference herein.

TECHNICAL FIELD

The present invention relates to: nanoparticles comprising aminoacyl tRNA synthetase and an anticancer composition comprising the same and, specifically, to nanoparticles comprising glycyl-tRNA synthetase (GRS), leucyl-tRNA synthetase (LRS), and isoleucyl-tRNA synthetase (IRS) and having anticancer or immunopotentiating activity; a pharmaceutical composition for preventing or treating cancer comprising the nanoparticles as an active ingredient; and a method for preparing the nanoparticles.

BACKGROUND ART

Membrane-bound vesicles and particles including exosomes, ectosomes, microvesicles, and secretory lysosomes are recognized as means for transportation along non-classical secretory pathways. Various types of cells, such as cancer and immune cells, have been shown to release diverse vesicles so as to mediate cell-to-cell communications. Although secreted vesicles as above are defined differently depending on their biogenesis, secretory mechanisms, and functions, the classification of these particles is not clearly defined (established) as of now.

Aminoacyl-tRNA synthetase (ARS) is an enzyme that attaches a specific amino acid onto its corresponding tRNA. In higher organisms, the aminoacyl-tRNA synthetases include 23 types of enzymes, including three types involved in the formation of multisynthetase complex, such as AIMP1 (p43), (AIMP2)p38, and (AIMP3)p18, besides 20 types of enzymes according to the respective kinds of amino acids. Except for the enzymes involved in the formation of multisynthetase complex, some enzymes are present in a free form. The aminoacyl-tRNA synthetases have been recently reported to have basic functions and various other activation functions under particular environments, one of which is an effect of promoting an apoptosis of particular cancer cells by glycyl-tRNA synthetase (GRS), leucyl-tRNA synthetase (LRS), isoleucyl-tRNA synthetase (IRS) and the like.

However, their apoptosis-inducing activity has been known, while their secretory mechanisms have still not been revealed.

DETAILED DESCRIPTION OF THE INVENTION

Technical Problem

While investigating on ARS secretory mechanisms, the present inventors have found nanoparticles comprising ARS which possess characteristics distinctive from those of exosomes and are remarkably effective in the apoptosis of cancer cells, and thus completed the present invention.

Therefore, an aspect of the present invention is to provide nanoparticles comprising glycyl-tRNA synthetase (GRS), leucyl-tRNA synthetase (LRS), and isoleucyl-tRNA synthetase (IRS) and possessing an activity of treating cancer or enhancing immune function.

Another aspect of the present invention is to provide a pharmaceutical composition for preventing or treating cancer, the composition comprising the nanoparticles as an active ingredient.

Still another aspect of the present invention is to provide a method for preventing or treating cancer, the method comprising administering an effective amount of the nanoparticles to a subject in need thereof.

Another aspect of the present invention is to provide use of the nanoparticles for preparing an agent for preventing or treating cancer.

Still another aspect of the present invention is to provide a pharmaceutical composition for enhancing immune function, the composition comprising the nanoparticles as an active ingredient.

Another aspect of the present invention is to provide a method for enhancing immune function, the method comprising administering an effective amount of the nanoparticles to a subject in need thereof.

Still another aspect of the present invention is to provide use of the nanoparticles for preparing an agent for enhancing immune function.

Further still another aspect of the present invention is to provide a method for preparing the nanoparticles, the method comprising: (a) applying apoptotic stress to cells; and (b) collecting nanoparticles secreted from the cells in step (a).

Another aspect of the present invention is to provide a method for preparing the nanoparticles, the method comprising: (a) co-culturing cells and cancer cells; and (b) collecting nanoparticles secreted from the cells in step (a).

Technical Solution

In accordance with an aspect of the present invention, there are provided nanoparticles comprising glycyl-tRNA synthetase (GRS), leucyl-tRNA synthetase (LRS), and isoleucyl-tRNA synthetase (IRS) and possessing an activity of treating cancer or enhancing immune function.

In accordance with another aspect of the present invention, there is provided a pharmaceutical composition for preventing or treating cancer, the composition comprising the nanoparticles as an active ingredient.

In accordance with another aspect of the present invention, there is provided a method for preventing or treating cancer, the method comprising administering an effective amount of the nanoparticles to a subject in need thereof.

In accordance with still another aspect of the present invention, there is provided use of the nanoparticles for preparing an agent for preventing or treating cancer.

In accordance with another aspect of the present invention, there is provided a pharmaceutical composition for enhancing immune function, the composition comprising the nanoparticles as an active ingredient.

In accordance with still another aspect of the present invention, there is provided a method for enhancing immune function, the method comprising administering an effective amount of the nanoparticles to a subject in need thereof.

In accordance with another aspect of the present invention, there is provided use of the nanoparticles for preparing an agent for enhancing immune function.

In accordance with still further another aspect of the present invention, there is provided a method for preparing the nanoparticles, the method comprising: (a) applying apoptotic stress to cells; and (b) collecting nanoparticles secreted from the cells in step (a).

In accordance with another aspect of the present invention, there is provided a method for preparing the nanoparticles, the method comprising: (a) co-culturing cells and cancer cells; and (b) collecting nanoparticles secreted from the cells in step (a).

Hereinafter, the present invention will be described in detail.

The present invention provides nanoparticles comprising glycyl-tRNA synthetase (GRS), leucyl-tRNA synthetase (LRS), and isoleucyl-tRNA synthetase (IRS) which possess an activity of treating cancer or enhancing immune function.

The nanoparticles according to the present invention are characterized in that particular aminoacyl-tRNA synthetases (ARS), i.e., GRS, LRS, and IRS, are contained in the particles. As used herein, the nanoparticles of the present invention are exchangeably designated as "ARS-SP" or "SNAP".

As used herein, the GRS, LRS, and IRS includes not only natural or recombinant types of human GRS, LRS, and IRS, but also non-human homologues of the human GRS, LRS, and IRS.

Specifically, as used herein, the amino acid sequence of the GRS is not particularly limited as long as the GRS is a polypeptide known as a glycyl-tRNA synthetase in the art. For instance, the GRS may comprise the amino acid sequence of SEQ ID NO: 1, and include its functional equivalents.

As used herein, the amino acid sequence of the LRS is not particularly limited as long as the LRS is a polypeptide known as a leucyl-tRNA synthetase in the art. For instance, the LRS may comprise the amino acid sequence of SEQ ID NO: 2, and include its functional equivalents.

As used herein, the amino acid sequence of the IRS is not particularly limited as long as the IRS is a polypeptide known as an isoleucyl-tRNA synthetase in the art. For instance, the IRS may comprise the amino acid sequence of SEQ ID NO: 3, and include its functional equivalents.

The term "functional equivalent" refers to a polypeptide having sequence homology (that is, identity) of at least 70%, preferably at least 80%, and more preferably at least 90% to the amino acid sequences of the GRS, LRS, and IRS, respectively. For example, the functional equivalent thereof includes a polypeptide having sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%, and refers to a polypeptide exhibiting a substantially identical physiological activity to the polypeptide represented by SEC ID NO: 1 (GRS), SEQ ID NO: 2 (LRS), or SEQ ID NO: 3 (IRS). As used herein, the term "substantially identical physiological activity" refers to an activity of inhibiting cancer cells or inducing the death of cancer cancer cells. The functional equivalent may be formed as a result of addition, substitution, or deletion of a part of each of the amino acid sequences of the GRS, LRS, and IRS, respectively. As used herein, the substitution of the amino acid is preferably a conservative substitution. Examples of the conservative substitution of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). In addition, the functional equivalent includes variants in which some amine acids are deleted from each of the amino acid sequences of the GRS, LRS, and IRS. The deletion or substitution of amino acids is preferably located at a region that is not directly associated with the physiological activity of the polypeptide of the present invention. Also, the deletion of amino acids is preferably located at a region that is not directly associated with the physiological activity of the polypeptide. In addition, the functional equivalent also includes variants in which some amino acids are added to either terminus of the amino acid sequence of the polypeptide or inserted into the amino acid sequence of the polypeptide. In addition, the functional equivalent as used in the present invention also includes polypeptide derivatives in which the chemical structure of the polypeptide is partially modified while a basic backbone of the polypeptide of the present invention and its physiological activity are maintained. Examples of such a modification include structural modifications for changing the stability, storability, volatility, or solubility of the polypeptide according to the present invention.

Preferably, in the GRS which is included in the nanoparticles according to an aspect of the present invention, some of its amino acid residues may be palmitoylated. As used herein, the term "palmitoylation" may used exchangeably with the terms "palmitoylating/palmitoylated" and "palmitoylation reaction", and refers to a reaction in which a fatty acid such as palmitic acid is covalently linked to a cysteine residue of a protein. Preferably, the GRS, which is included in the nanoparticles according to an aspect of the present invention, may be one in which the 390th amino acid residue of cysteine in the amino acid sequence of SEQ ID NO: 1 is palmitoylated. While the GRS is fixed on a surface of the nanoparticle according to an aspect of the present invention through palmitoylation, the manufacturing yield from cells and the effects of the nanoparticles according to the present invention are influenced due to such a palmitoylation. In addition, the GRS included in the nanoparticles according to the present invention may be one in which its 471st residue of cysteine in the amino acid sequence of SEQ ID NO: 1 is further palmitoylated.

The nanoparticles (i.e., ARS-SP) according to the present invention are characterized by being lipoprotein-like particles, while their fundamental structures and morphological characteristics are very similar to chose of existing known lipoprotein particles.

As used herein, the term "lipoprotein" or "lipoprotein particle" may refer to a complex of a lipid and a protein in a broad sense, and more specifically, refers to a globular micelle-like particle composed of a non-polar core and a shell enclosing the core and comprising a polar material such as a protein and a phospholipid.

The fact that the nanoparticles according to the present invention function as a means to secrete ARS of GRS, LRS, and IRS extracellularly from cells and have similar morphological characteristics to lipoprotein particles is distinguishable from the previously known fact that secretory materials from cells are secreted as one type of microvesicles originating from the cellular membrane. Even though microvesicles (e.g., exosomes) and lipoproteins share common structural lipid components to some extent and significantly overlap each other in view of their particle size, there is a remarkable difference with respect to the particle structure and the isolation mechanism by their respective target tissues between the said two types of particles. It is generally known that the microvesicles from cells have a lipid bilayer structure, whereas the lipoprotein particles have a micelle-like, lipid single layer structure.

The nanoparticles of the present invention may have a diameter of preferably 10-70 nm and more preferably 20-50 nm.

In addition, the nanoparticles according to an aspect of the present invention may further comprise vimentin and insulin-like growth factor 2 receptor (IGF2R). The vimentin and IGF2R are known to assist the anticancer effects of ARSs (i.e., GRS, LRS, and IRS) included in the nanoparticles according to the present invention, thereby exhibiting a remarkably synergistic effect.

The nanoparticles according to the present invention may be an artificial construct through artificial complexation of the aforementioned components, while being preferably a natural construct that is generated from cells and secreted extracellularly under particular conditions (environments).

The ARS-SP nanoparticles according to the present invention, which may be a natural construct from cells, may function as a means to secrete GRS, LRS, and IRS from cells through a non-endoplasmic reticulum (ER)/Golgi pathway or a non-exosomal secretion pathway, while, at the same time, acting as a carrier for uptake into cancer cells.

Specifically, the present invention provides a method for preparing the nanoparticles (ARS-SP) according to the present invention, the method comprising: (a) applying apoptotic stress to cells; and (b) collecting nanoparticles secreted from the cells in step (a).

In step (a), the apoptotic stress is applied to cells in order to promote the production of GRS, LRS, and IRS and activate secretory mechanisms thereof.

As used herein, the cells may preferably include epithelial cells and immune cells. Specifically, the immune cells include, but are not limited to, T cells, NK cells, NKT cells, gamma delta cells, dendritic cells, monocytes, and macrophages. Most preferably, the cells may be monocytes or macrophages.

The macrophages are also called phagocytes, which is one type of immune cells. The macrophages are distributed over all types of tissues in the animal body, while being a generic term for large-sized amoeboid phagocytes that engulf and digest foreign substances, bacteria, viruses, in vivo waste cells, and the like.

As disclosed in Korean Patent Registration No. 10-1102485, the application of the apoptotic stress to macrophages is known to induce the production or GRS in the macrophages. Specifically, the apoptotic stress may be applied by the creation of apoptosis-inducing environments or the treatment with apoptosis-inducing substances. The apoptosis-inducing environments may include oxygen deficiency, glucose starvation, low pH, and excessive lactic acid, while being most preferably glucose starvation. The apoptosis-inducing substance may be selected from the group consisting of tumor necrosis factor-α (TNF-α), TNF-β, Fas ligand (Fas L), TNF-related apoptosis inducing ligand (TRAIL), Perforin, Bax, Bak, and adriamycin, while being most preferably Fas ligand or adriamycin.

In step (b), only nanometer-sized particles (i.e., ordinary nanoparticles) are isolated and obtained that are produced from the cells of step (a) and secreted extracellularly. The cell culture medium, which is cultured with apoptotic stress in step (a), is collected to provide nanometer-sized structure fractions (i.e., nanoparticle fractions) which are assumed as ARS-SP nanoparticles according to the present invention.

Methods for isolating and obtaining exclusively particles with desired size and density from mixtures are well known in the art. For instance, such a method includes density gradient (e.g., density gradient by ficoll, glycerol, sucrose, and OptiPrep™), centrifugation (e.g., ultracentrifugation, and density gradient centrifugation), filtration (e.g., a method using a filter with a particular diameter, such as gel filtration or ultrafiltration), dialysis, and free-flow electrophoresis. The particles with desired particle sizes may be obtained by repeatedly performing at least one of the several above mentioned methods several times.

In step (b), nanoparticles with a diameter of 10-70 nm are preferably obtained through the foregoing methods. Most preferably, nanoparticles with a diameter of 20-50 nm may be obtained.

Furthermore, the method for preparing nanoparticles (i.e., ARS-SPs) according to the present invention may further comprise, after step (b), any additional step for selectively isolating (or high-concentration purifying) ARS-SP nanoparticles from the nanoparticle fractions obtained in step (b).

The nanoparticle fractions with a predetermined size obtained by the aforementioned methods in step (b) may comprise not only desired ARS-SPs according to the present invention, but also vesicles with similar sizes and/or density. Out of the vesicles secreted from cells, exosomes are especially known to share common structural lipid components with lipoproteins, while their particle size of 30-100 nm significantly overlaps that of lipoproteins. Therefore, the preparation obtained in step (b) may comprise exosomes as a kind of impurity as well as ARS-SPs according to the present invention.

Therefore, the method for preparing nanoparticles (e.g., ARS-SPs) according to the present invention may further comprises step (c) of differentiating exosomes from nanoparticles (nanoparticle fractions) collected in step (b).

As used herein, the term "differentiation" of the exosomes in step (c) means some or all of the separation, fractionation, selection, exclusion, or removal of exosomes.

The differentiation of the exosomes may be performed by known exosome capture methods which may be for instance a capture method using an antibody or lectin specific to an exosome marker, but are not limited thereto. The exosome marker means a material which exists specifically only in exosomes and thus differentiates the exosomes from other cell structures. The kind of the exosome marker is not particularly limited as long as it is a known exosome marker, and examples thereof include syntenin-1, CD9, CD63, and CD81.

In addition, the present invention provides a method for manufacturing the nanoparticles (ARS-SP) of the present invention, the method including: (a) co-culturing cells and cancer cells; and (b) collecting nanoparticles secreted from the cells in step (a).

In step (a), the cells are co-cultured with cancer cells to induce the production of ARS in the cells (i.e., promoting the production of intracellular GRS, LRS, and IRS and activating secretory mechanisms thereof).

As used herein, the cells may preferably include epithelial cells and immune cells. Specifically, the immune cells include, but are not limited to, T cells, NK cells, NKT cells, gamma delta cells, dendritic cells, monocytes, and macrophages. Most preferably, the cells may be monocytes or macrophages.

The cancer cells are cells derived from tumor or cancer, and the kind of cancer cells are not particularly limited, but examples thereof may be at least one selected from the group consisting of breast cancer cells, colorectal cancer cells, lung cancer cells, gastric cancer cells, liver cancer cells, blood cancer cells, bone cancer cells, pancreatic cancer cells, skin cancer cells, head or neck cancer cells, cutaneous or intraocular melanoma cells, eye tumor cells, peritoneal cancer cells, uterine cancer cells, ovarian cancer cells, rectal cancer cells, anal cancer cells, colon cancer cells, fallopian tube carcinoma cells, endometrial carcinoma cells, cervical cancer cells, vaginal cancer cells, vulvar carcinoma cells, Hodgkin's disease cells, esophageal cancer cells, small intestine cancer cells, endocrine cancer cells, thyroid cancer cells, parathyroid carcinoma cells, adrenal cancer cells, soft tissue sarcoma cells, urethral cancer cells, penile cancer cells, prostate cancer cells, testicular cancer cells, oral cancer cells, gallbladder cancer cells, cholangiocarcinoma cells, leukemia cells, lymphocyte lymphoma cells, bladder cancer cells, kidney cancer cells, ureteral cancer cells, renal cell carcinoma cells, renal pelvic carcinoma cells, CNS tumor cells, primary CNS lymphoma cells, spinal cord tumor cells, brain stem glioma cells, and pituitary adenoma cells.

The co-culture may preferably be performed in serum-free media in vitro.

In step (b) as described above, only nanometer-sized particles (meaning ordinary nanoparticles), which are produced from the cells of step (a) and secreted extracellularly, are isolated and obtained. In the similar manner, the method for preparing nanoparticles may further comprises the above described step (c) of differentiating exosomes from nanoparticles (nanoparticle fractions) collected in step (b).

The nanoparticles (ARS-SPs) of the present invention have an excellent anticancer effect. In an embodiment of the present invention, it was confirmed that ARS-SPs, which were obtained from macrophages via the aforementioned series of steps, possess an excellent anticancer effect in vitro and in vivo.

Therefore, the present invention provides provide a pharmaceutical composition for preventing or treating cancer, the composition comprising the nanoparticles as an active ingredient.

In addition, the present invention provides a method for preventing or treating cancer, the method comprising administering an effective amount of the nanoparticles to a subject in need thereof.

In addition, the present invention provides use of the nanoparticle for preparing an agent for preventing or treating cancer.

The anticancer composition according to the present invention is very effective in the treatment of cancer. Examples of the cancer include, but are not limited to, breast cancer, colorectal cancer, lung cancer, small cell lung cancer, gastric cancer, liver cancer, blood cancer, bone cancer, pancreatic cancer, skin cancer, head or neck cancer, cutaneous or intraocular melanoma, eye tumor, peritoneal cancer, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, urethral cancer, penile cancer, prostate cancer, testicular cancer, oral cancer, gallbladder cancer, cholangiocarcinoma, chronic or acute leukemia, lymphocyte lymphoma, bladder cancer, kidney cancer, ureteral cancer, renal cell carcinoma, renal pelvic carcinoma, CNS tumor, primary CNS lymphoma, spinal cord tumor, brain stem glioma, and pituitary adenoma.

In addition, the nanoparticles (ARS-SP) according to the present invention are characterized by having an autocrine action on macrophages, and enhancing the immunity of hosts by increasing M1 polarization of macrophages. Specifically, the nanoparticles according to the present invention can enhance immune function by activating the phagocytic activity of macrophages and increasing the secretion of immune cytokines, such as TNF-α and IL-6.

Therefore, the present invention provides a pharmaceutical composition foe enhancing immune function, the composition comprising the nanoparticles as an active ingredient. The nanoparticles of the present invention prepared as described above are characterized by having Arp2/3 complex, which has been previously known to play an important role in the phagocytic activity of macrophages. In an embodiment of the present invention, the immunity-enhancing effect of ARS-SP nanoparticles according to the present invention and related factors have been described.

In addition, the present invention provides a method for enhancing immune function, the method comprising administering an effective amount of the nanoparticles to a subject in need thereof.

In addition, the present invention provides use of the nanoparticles for preparing en agent for enhancing immune function.

Herein, the pharmaceutical composition may be formulated appropriately together with pharmaceutically acceptable carriers. The term "pharmaceutically acceptable" composition refers to a composition that is physiologically acceptable and does not cause allergic reactions such as gastrointestinal disorder and vertigo, or similar reactions, when administered to humans. Examples of the pharmaceutically acceptable carriers may include carriers for oral administration, such as lactose, starch, cellulose derivative, magnesium stearate, and stearic acid, and carriers for parenteral administration, such as water, suitable oil, saline solution, aqueous glucose, and glycol, while it may further include a stabilizer and a preservative. Examples of suitable stabilizers include antioxidants such as sodium hydrogen sulfite, sodium sulfite, and ascorbic acid. Examples of suitable preservatives include benzalkonium chloride, methyl- or propyl-paraben, and chlorobutanol. The following literature may be referred to for other pharmaceutically acceptable carriers (Remington's Pharmaceutical Sciences, 19th ed., Mack Publishing Company, Easton, Pa., 1995).

The pharmaceutical composition of the present invention may be formulated into a dosage form for oral administration, but is not limited thereto. The nanoparticles according to the present invention and pharmaceutically acceptable salts may be mixed with excipients to be formulated in the form of an ingestible tablet, buccal tablet, troche, capsule, elixir, suspension, syrup, wafer, and the like. These preparations may also contain diluents (e.g., lactose, dextrose, sucrose, mannitol, sorbitol, cellulose and/or glycine), lubricants (e.g., silica, talc, stearic acid and a magnesium or calcium salt thereof, and/or polyethylene glycol), in addition to active ingredients. The tablets may also contain binders, such as magnesium aluminum silicate, starch pastes, gelatin, tragacanth, methylcellulose, sodium carboxymethylcellulose, and/or polyvinylpyrrolidone, and, if desired, may further contain disintegrating agents, such as starch, agar, or alginic acid or a sodium salt thereof, absorbents, colorants, flavors, and/or sweeteners. The dosage form may be prepared by ordinary mixing, granulation, or coating. An injectable dosage form may be prepared according to techniques well known in the art by using a suitable dispersant or humectant and a suspension agent. For example, respective ingredients may be formulated into an injectable preparation by being dissolved in saline or buffer. For preparations for parental administration, the respective ingredients may be formulated in the form of an injection, a cream, a lotion, an ointment for external application, an oil, a moisturizer, a gel, an aerosol, and a nasal inhaler, by the method known in the art. These dosage forms are described in the literature, which is generally known in pharmaceutical chemistry (Remington's Pharmaceutical Science, 15th Edition, 1975. Mack Publishing Company, Easton, Pa. 18042, Chapter 87: Blaug, Seymour).

The pharmaceutical composition formulated by the method above may be administered at an effective amount through various routes including oral, percutaneous, subcutaneous, intravenous, and intramuscular routes. As used herein, the term "effective amount" refers to the amount that cause the effect of treating cancer or enhancing immune function, upon being administered to a patient. As used herein, the term "subject" refers to an animal, preferably mammals, particularly animals including human beings. It may include cells, tissues, and organs which are originated from an animal. The subject may be a patient in need of treatment. As used herein, the term "subject in need thereof" includes a subject in need of preventing or treating cancer, or a subject in a state of decreased immune function.

The pharmaceutical composition of the present invention may be administered in itself alone or as various forms of preparations as mentioned above. Preferably, the pharmaceutical composition may be administered until a desired effect (i.e., an effect of treating cancer or enhancing immune function) is achieved. The pharmaceutical composition of the present invention may be administered through various routes by a method known in the art. That is, the pharmaceutical composition may be administered orally or parenterally, for example, intrabuccally, intramuscularly, intravenously, intracutaneously, intraarterialy, intramarrowly, subduraly, intraperitonealy, intranasally intravaginally, intrarectally, sublingually, or subcutaneously, or into gastrointestinal tracts, mucosal layers, or respiratory organs. Also, the pharmaceutical composition of the present invention may be administered by binding to molecules that induce highly affinitive binding to target cells or tissues (e.g., skin cells or tissues) or in a form of being capsulated in the molecules. The pharmaceutical composition of the present invention may bind to sterols (e.g., cholesterols), lipids (e.g., cationic lipids, virosomes, or liposomes), ox target cell specific binders (e.g., ligands recognized by target cell specific receptors). Examples of suitable coupling agents or cross-linking agents may include protein A, carbodiimide, and N-succinimidyl-3-(2-pyridyldithio)propionate (SPDP).

In the pharmaceutical composition of the present invention, a total effective amount of the nanoparticles according to the present invention may be administered to a subject as a single dose, or as multiple doses by the fractionated treatment protocol for a long-period administration. While the pharmaceutical compositions of the present invention may contain an active ingredient in its various amount depending on the administration purpose, it may typically be administered several times a day at an effective dose of 0.1 ug to 1 g per each administration. However, the effective dose for each subject may be suitably determined by considering various factors, such as age, body weight, health condition, sex, disease severity, diet, and excretion of a subject in need of treatment, as well as administration route and the number of administration. Therefore, in consideration of these facts, a skilled person having ordinary skill in the art can determine an appropriate effective dose according to the administration purpose. The pharmaceutical composition of the present invention is not particularly limited with respect to the dosage form, route of administration, and administration method as long as the effect of the present invention is accomplished.

Advantageous Effects

As described above, the present invention provides nanoparticles comprising glycyl-tRNA synthetase (GRS), leucyl-tRNA synthetase (LRS), and isoleocyl-tRNA synthetase (IRS) and possessing the activity of treating cancer or enhancing immune function; a pharmaceutical composition for preventing or treating cancer, the composition comprising the nanoparticles as an active ingredient; and a method for preparing the nanoparticles. The nanoparticles and the composition comprising the same are effective in preventing or treating cancer.

BRIEF DESCRIPTION OF THE DRAWINGS

FIG. 3b illustrates the confirmatory results of the presence of exosome markers (ALB, ANXA2, CD63, CD81, CD9, PDCD6IP, SDCBP, YWHAE, YWHAZ) from ARS-SP (SNAP) according to the present invention.

FIG. 5 illustrates the results of immune-gold staining and 3D tomography of GRS, indicating that, when macrophages were treated with ARS-SPs according to the present invention (indicated as SNAPs), the ARS-SP nanoparticles were absorbed into the macrophages by endocytosis (PM: plasma membrane).

FIG. 12b illustrates the anticancer effect (cytotoxic effects) of ARS-SP on several cancer cell lines when various cancer cell lines were treated with ARS-SPs (SNAPs) or GRS.

FIG. 13a illustrates the results of the frequency of tumors having a volume of 100 $mm^3$ or more within 15 days in the test group (a total of six mice) when H460 cells ($7.5 \times 10^6$), together with ARS-SPs (SNAPs, 6 mg/kg) or GRS (6 mg/kg) were subcutaneously injected to the flank of BALB/c nude mice (tumor initiation model).

FIG. 13b illustrates the tumor volume measurement results of the test groups and the control 15 days after H460 cells ($7.5 \times 10^6$), together with ARS-SPs (SNAPs) or GRS (6 mg/kg) were subcutaneously injected to the flank of BALB/c nude mice (tumor initiation model).

MODES FOR CARRYING OUT THE INVENTION

Figure 1A:
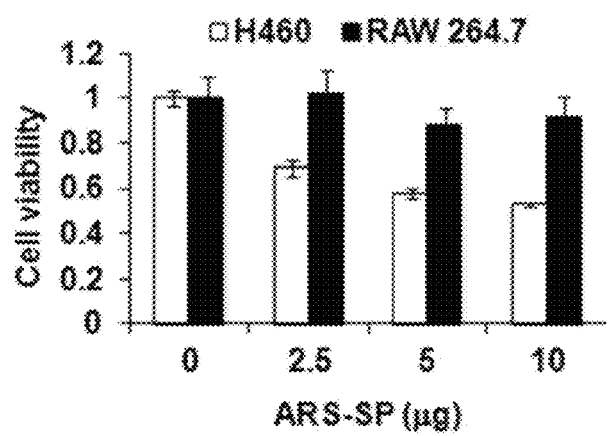
FIG. 1a illustrates MTT assay results of cell viability when cancer cells (H460) and macrophages (RAW264.7) were treated with ARS-SPs according to the present invention in different amounts for 24 h, confirming the anticancer effect of ARS-SP (Error bar indicates mean±standard deviation from average three times of repeated tests).

Hereinafter, the present invention will fee described in detail.

However, the following examples are merely for illustrating the present invention and are not intended to limit the scope of the present invention.

<Method>

1. Cell Culture and Reagents

RAW264.7 cells were grown in DMEM containing 10% FBS, 50 mg/ml streptomycin, and penicillin. H460 cells were grown RPMI 1640 medium containing 10% FBS, 50 mg/ml streptomycin, and penicillin. Among primary antibodies against respective antigens, syntenin-1 (S-31) was obtained from Santa Cruz Biotechnology, with gp96 (9G10) from Enzo life sciences, GRS from Abcam, and tubulin (TUB 2.1) from Sigma. Among secretory pathway inhibitors, brefeldin A, probenicid, sodium azide, monymycin, methyl-beta-cyclodextrin, and 2-bromo-palmitate were purchased from Sigma and Calbiochem, respectively.

2. Dynamic Light Scattering

The secreted particles were obtained and resuspended in PBS. The particle size was measured by light scattering spectrophotometer ELS-Z (Otsuka Electronics, Japan). Measurement was performed in automatic mode after equilibration for 5 min at 20° C. Data were processed with the manufacturer's software in multiple narrow modes.

3. Sucrose Density Gradient Centrifugation

To determine the density of particles, 100,000 g pelleted particles were overlaid onto a continuous sucrose density gradient and centrifuged at 150,000 g for 15 hr. Eight fractions were collected, assayed for density by refractometry, and resuspended in SDS-PAGE sample buffer, and then immunoblotted using specific antibodies.

4. Electron Microscopic Observation of Secreted Particles

For negative staining, isolated ARS-SPs were diluted 5-fold in PBS, of which 5 μl was then applied to a glow-discharged carbon-coated grid (Harriett Plasma, USA) for 3 min in air, and the grid was negatively stained using 1% uranyl acetate (see Jung, H. S., et. al., *Mol. Biol. Cell:* 19; 3234-3242, 2008). The same procedure was used for all samples. For cryo-electron microscopy, 5 μl of sample solution was suspended onto the copper R1.2/1.3 Quantifoil EH grids (SPI Supplies) that were pre-treated in air for 30 sec (in air). The grids were then blotted and frozen using an FEI Vitrobot, MarkI (FEI) with the setting of 100% humidity, 4° C. and blot time of 2.5 s. The vitreous ice sample grids were maintained at a temperature of around −177° C. within an electron microscope using a aide-entry Gatan 626 cryo holder (Gatan). For immuno-electronic microscopy, ARS-SPs were mixed with anti-GRS antibody for 6 hr, and then were allowed to bind with secondary antibody conjugated with 6 nm gold particles (JIRE, U.K.) (immuno-gold labeling). Thereafter, the mixture was left on ice for 12 hr, and then negatively stained as described above. The grids were tested using a Technai G2 spirit Twin TEM (FEI, USA) operated at 120 kV. Images were recorded on 4K×4K Ultrascan 895 CCD (Gatan, U.S.) at a nominal magnification of 40,000 and under-focus values ranging from 2 to 3.

5. Election Tomography

Electron tomography was performed on immuno-gold-labeled ARS-SP localized close to the cell membrane. Sample images inclined from −60° to +60° were recorded by 2° increase and the images were magnified to ×50,000 by using the megapixel CCD camera (JEOL, Tokyo, Japan). An automated data obtainment for electron tomography was conducted using Recorder module of TEMography suite (System in Frontier Inc., Tokyo, Japan). Image alignment, reconstruction, 3D volume rendering, and visualization were conducted using Composer and Visualizer module of TEMography, while the IMOD software package was partially used.

6. Mass Spectrometry

Secreted particles isolated from RAW264.7 cells, which were cultured in glucose-containing and glucose-deprived media as described above, were precipitated with anti-GRS antibodies. The proteins separated from the particles were separated by SDS-PAGE and digested by in-gel trypsin digestion process. Tryptic fragments were separated by reversed-phase chromatography for each run and electrospray-ionized. For reversed-phase chromatography, Eazy nano LC II autosampler (Thermo Scientific) with reversed-phase peptide trap EASY-Column (100 μm inner diameter, 2 cm length) and reversed-phase analytical EASY-Column (75 μm inner diameter, 10 cm length, 3 μm particle size, Thermo Scientific) was used. Electrospray ionization was performed using a 30 μm nano-bore stainless steel online emitter (Thermo Scientific) set at a voltage of 2.6 V and a flow rate of 300 nl/min. The chromatography system was coupled online with an LTQ Velos Orbitrap mass spectrometer (Thermo Scientific) equipped with an ETD source. A mass spectrometry (MS) intensity-based label-free quantitation was performed using PE-MMR as known previously. Briefly, during PE-MMR analysis, MS features of a peptide, which emerged over a period of LC elution time in LC-MS/MS, were grouped into a unique mass class (UMC). Peptide abundance for each UMC was calculated as the abundance summation of all mass spectral components of the UMC. In order to identify peptide ID for the UMC, DTA file was linked to the UMC by matching the UMC mass with the precursor mass in the DTA. When peptide ID was identified for the linked DTA file with false positive rate of 1% after MS-GF$^+$ search and target-decoy analysis, the peptide ID was assigned to the UMC. The UMCs across the replicates were aligned using the peptide IDs and normalized over elution times. By using all the aligned peptides, the proteins were selected, as highly reliable proteins, which have at least two non-redundant peptides and a maximum intensity of at least $10^5$. Among them, 90 proteins each of which has at least one non-redundant peptide unique to the protein were identified as the proteins predominant in ARS-SPs.

7. Palmitoylation Mass Analysis

Protein analysis was performed using the Proteome Discoverer v 1.3 database search engine (Thermo scientific), while searches were performed on IPI. mouse. v 3.87 database. The search parameters were set at a fragment mass tolerance of 0.6 Da, peptide mass tolerance of 25 ppm and maximum missed cleavage of 2. The results were filtered by peptide rank (maximum rank: 1), peptide number per protein (minimal number of peptides: 2) and charge state versus score (minimal XCorr score for charge state=+1: 1.7, +2: 2.5, +3: 3.2, >+4: 3.5). The carbamidomethylation (+57.021 Da) of cysteine (C) and deamidation (+0.984 Da) of asparagine or glutamine (N, Q) were set as a static or variable modification, respectively. The processed data were transformed to the sf file using Scaffold 3 program, while all the modified peptides identified from the control or glucose-starved samples were scored and compared using Scaffold PTM software.

8. Similarity Test

Exosome protein profiles of 12 different sample types were obtained from ExoCarta. For the discrete comparison, samples with more than 100 identified proteins were only used. Similarity scores for each experiment were calculated using Jaccard similarity coefficient.

$$similarity=h(P_x)*h(P_g)/\{|h(P_x)|+|h(P_g)|-h(P_x)*h(P_g)\}$$

$|h(P_x)|$ and $|h(P_g)|$ are the counts of proteins in exosome and and ARS-SP respectively. $h(P_x)*h(P_g)$ represents the number of proteins shared by two group. The average score for each sample was calculated and used.

9. Chemical Fixation and Electron Microscopy

After H460 cells were cultured with the isolated ARS-SPs, the samples were fixed in a mixture of 2% glutaraldehyde in 25 mM phosphate buffer solution (pH 7.2) fox 1, followed by post fixation in 2% $OsO_4$ in 25 mM phosphate buffer solution (pH 7.2) for 2 hr. After rinsing off the phosphate buffer solution, the samples were dehydrated in ethanol and embedded in Epon. Ultrathin sections (80 nm thickness) were cut on an ultracut-S microtome (Leica), collected on copper grids, and stained in uranyl acetate and lead citrate. The stained sections were examined by electron microscopy.

10. Cell Viability Assay

H460 and RAW264.7 cells ($5\times10^3$) seeded in the 96 well plate were cultured for 24 hr, and then treated With ARS-SPs (10 μg/ml) or GRS (100 nM). MTT (USB) solution (5 mg/ml) was added to each well (final concentration; 0.5 mg/ml) which was additionally cultured for 4 hr. After removing medium, the MTT formazan crystals were dissolved in 100 ml of DMSO (Sigma). The absorbance was measured at 570 nm with the microplate reader (TECAN). In order to investigate the neutralizing effect of anti-GRS antibody, the isolated ARS-SPs were pre-incubated with the anti-GRS antibody for 30 min and added to cells.

11. Metabolic Labeling Palmitoylation Assay

RAW264.7 cells were pre-cultured with glucose-containing DMEM for 1 hr and labeled with 0.1 mCi/ml (3H) palmitate (PerkinElmer) for 2 hr. In order to confirm GRS modifications, the cells were cultured in glucose-deprived DMEM containing [3H] palmitate for 2 hr. The cell lysates extracted by RIPA buffer were immunoprecipitated with anti-GRS antibodies. The radiolabeled-palmitoylated GRS was detected by scintillation counter.

12. Biotinylation of Surface of GRS-SPs

Isolated ARS-SPs were cultured with EZ-link Sulfo-NHS-LC-Biotin (Thermo) at 0.5 mg/ml at 4° C. for 30 min. In order to stop the biotinylation reaction, tris-HCL (pH 7.5) was added to a final concentration of 100 nM. In order to determine the localization of GRS in the particles, the biotinylated lipid particles were precipitated with streptavidin-sepharose bead (GE healthcare). After washing three times, the precipitates were dissolved and separated by SDS-PAGE for immunoblotting.

13. Xenograft Mice Model

Xenograft experiments were performed in accordance with the University Animal Care and Use Committee guidelines of Seoul National University. H460 cells ($7.5\times10^6$) were injected subcutaneously into the left flank of 8-week-old BALB/c female nude mice. The tumor growth was monitored and the tumor volume was measured using a caliper. The tumor volume was determined as length× $width^2\times0.52$. The treatment with test substances was initiated when the average tumor volume of each group reached 90-100 $mm^3$. Purified GRS or ARS-SPs were administrated via intravenous injection in a single dosage of 6 mg/kg/day for 4 days, while control group mice were injected with PBS. The tumor weights were measured on the day of sacrificing chose mice.

For the tumor initiation model, the nude mice were treated with GRS or ARS-SPs (6 mg/kg), followed by a subcutaneous injection of H460 cells. On day 15 after the tumor implantation (subcutaneous injection), the tumor volume and weight were measured.

14. Multiplex ELISA Assay

RAW264.7 cells were cultured in the 12 well plate. GRS or ARS-SPs were added at different concentrations to media. After culture for 6 hr, the media were collected, and spun down by centrifugation at 3,000 g for 10 min. Secreted TNF-α and IL-10 were detected using the ELISA kit (BD Science) according to the manufacturer's protocol. The samples were measured using the microplate reader (TECAN). In order to perform multiplex assay, the beads in which TNF-α, IL-6, RANTES, IL-1β, IL-12, IL-10, MMP-9, INF-γ, MIP-3α, and CXCL10 were previously mixed were purchased from R&D Science. The standard group and the samples were treated with the beads, and cultured in the plate shaker for 2 hr. Subsequently, each well was treated with secondary antibodies. After culture for 1 hr, the streptavidin-PE solution was added, followed by further culture for 30 min. The beads were measured by the luminex system (BioPad, Bioplex 200), and analyzed by the bioplex software (BioRad 6.0).

15. Measurement of Phagocytosis of Macrophages

The phagocytic activity of macrophages was measured using the Vybrant Phagocytosis Assay Kit (Invitrogen). Briefly, RAW264.7 cells were seeded in the 96 well plate. The cells were treated with ARS-SPs, GRS, or LPS for 12 hr. After the treatment, the cells were further cultured together with fluorescein-labeled phagocytosis beads for 2 hr. Then, the phagocytic activity was quantified by quenching the extracellular fluorescence using Trypan blue and measuring the fluorescence intensity using the microplate reader (BMG Labtech, FLUOstar OPTIMA).

16. Intravital Phagocytosis Imaging

The effect of ARS-SP or GRS on the phagocytosis of macrophages in vivo was observed by customized laser-scanning confocal microscopy. For the implementation of 2D scanning, the fast-rotating polygonal mirror (Lincoln Laser) and galvanometer (Cambridge Technology) were used. In order to simultaneously detect three fluorescent signals. High-sensitive photomultiplier tubes (Hamamatsu) were equipped (utilized). Three detection channels were divided by dichroic mirrors (Semrock) and bandpass filters (Semrock). Electric signals obtained from PMT were digitalized by the 8-bit 3-channel frame grabber (Matrox). After images were taken from imaging systems, 512×512 pixel images were XY-shift compensated by Matlab (Mathworks), and reconstructed on one of two, XZ/YZ, by ImageJ software. Per in vivo phagocytosis imaging, male LysM-GFP (Lysozyme M-GFP) mice aged 18-22 week were used. The mice were anesthetized with a mixture of Zoletil (30 mg/kg) and xylazine (10 mg/kg). ARS-SPs (1 mg) or GRS (1 mg) conjugated to Alexa-405 (Life Technologies) was intradermally injected into the ear skin of mice using 31G microinjector (Hamilton). Six hours after the treatment, Alexa-594-conjugated phagocytosis bioparticles (Life technologies) were injected to a location where ARS-SPs or GRS had been injected. Phagocytosis was then visualized by confocal microscopy platform for 90 min.

17. qRT-PCR

Through conventionally known methods, the total RNA was extracted from the cells which had been completed with sample treatment, followed by the synthesis of cDNAs. Briefly, qRT-PCR was conducted using QRTPCR (Life Technology 7500) with cDNA template and forward and reverse primers as listed on table 1. A total of 40 cycles of the two-step reaction (95° C.-15 s and 54° C.-60 s) was conducted using The QRTPCR (Life Technology 7500) with 7500 Software 2.0.4., and the results were calculated by the relative quantification $\Delta\Delta C_T$ method.

TABLE 1

| Target | direction (5'-3') | sequence | SEQ ID NO |
|---|---|---|---|
| iNOS | Forward | CAGCTGGGCTGTACAAACCTT | 4 |
| | Reverse | CATTGGAAGTGAAGCGTTTCG | 5 |
| Arginase II | Forward | AAGAAAAGGCCGATTCACCT | 6 |
| | Reverse | CACCTCCTCTGCTGTCTTCC | 7 |
| TNF-alpha | Forward | CTCAAAATTCGAGTGACAAGCCTG | 8 |
| | Reverse | ATCGGCTGGCACCACTAGTT | 9 |
| IL-10 | Forward | AGACTTTCTTTCAAACAAAGGA | 10 |
| | Reverse | ATCGATGACAGCGCCTCAG | 11 |

EXAMPLE 1

In Vitro Anticancer Effect of Nanoparticles Secreted from Macrophages

<1-1> Obtaining of Nanoparticles Secreted in Glucose-Deprived Condition

RAW 264.7 cells were cultured in glucose-deprived DMEM medium (4 hr). Subsequently, the medium was centrifuged twice at 500 g (10 min) and 10,000 g (15 min) to remove cell debris, and then centrifuged at 100,000 g (120 m) to give pellet lipid particles.

<1-2> Verification on In Vitro Anticancer Effect

In order to investigate the anticancer effect of the nanoparticles obtained in Example 1-1, H460 and RAW 264.7 cells were treated with the obtained nanoparticles to determine their viability, respectively.

Figure 1B:
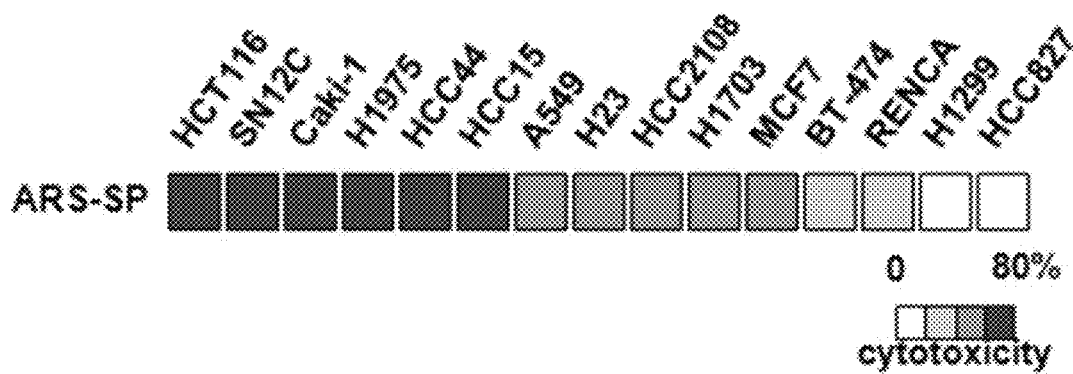
FIG. 1b illustrates the anticancer effect (cytotoxic effects) of ARS-SP according to the present invention on several cancer cell lines when various cancer cell lines were treated with 10 μg/ml of ARS-SPs for 48 h.

As a result, it was found that, on the contrary to that of RAW264.7 cells, the viability of H460 cells was decreased by the treatment of with the nanoparticles in a dose-dependent manner (FIG. 1a). In addition, 15 different cancer cell lines (HCT116, SN12C, Caki-1, H1975, HCC44, HCC15, A549, H23, HCC2108, H1703, MCF7, BT-474, RENCA, H1299, and HCC927) were treated with the nanoparticles to measure their cell viability, confirming that the nanoparticles showed a broad range of cytotoxicity (FIG. 1b).

EXAMPLE 2

In Vivo Anticancer Effect of Nanoparticles Secreted from Macrophages

Figure 2A:
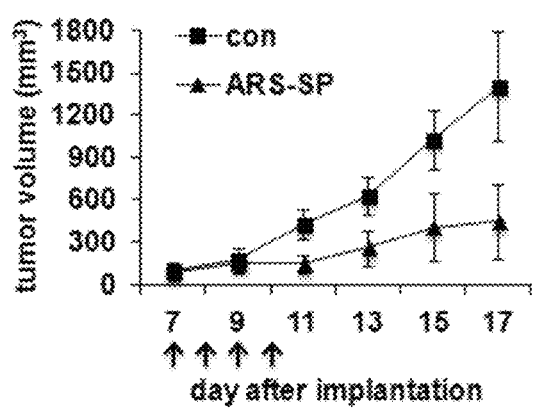
FIG. 2a illustrates a change in tumor volume over time after xenograft mouse models were treated with ARS-SPs according to the present invention at a dose of 6 mg/kg/day once a day for 4 days (arrows indicate the date when PBS (control) or ARS-SPs were injected into xenograft mouse models).
Figure 2B:
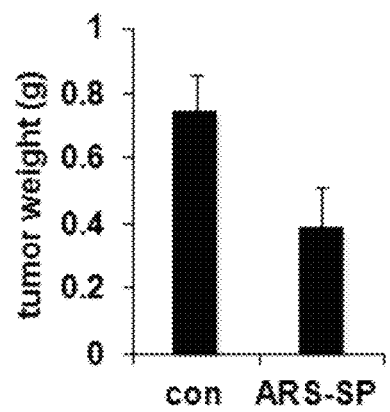
FIG. 2b illustrates tumor weight of xenograft mouse models, which were treated with ARS-SPs according to the present invention at a dose of 6 mg/kg/day once a day for 4 days and then sacrificed on day 17 of the mouse model construction.
Figure 2C:
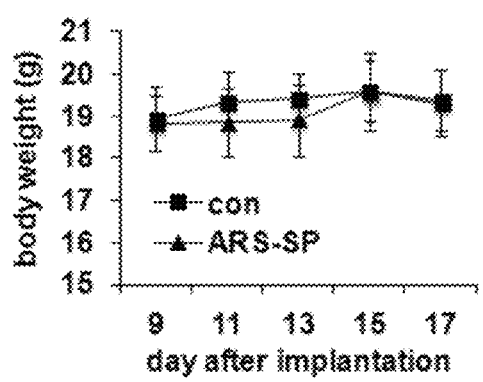
FIG. 2c illustrates a change in body weight over time of mouse models alter the xenograft mouse models were treated with ARS-SPs according to the present invention at a dose of 6 mg/kg/day once a day for 4 days.

In order to investigate whether the nanoparticles obtained in Example 1-1 also possess an in vivo anticancer effect, the nanoparticles were administered into xenograft mice. H460 cells were injected into BALB/c mice and then grown for 7 days. When tumors were grown to an average size of 90 mm³, the nanoparticles (6 mg/kg/dose) were injected by intravenous route once a day for 4 days. PBS was used as control. Compared with the control, the nanoparticle-treated tumor volume (FIG. 2a) and weight (FIG. 2b) were reduced by 68% and 48%, respectively. The lack of change in the weight and posture of the tested animals suggested no nanoparticle-induced overt toxicity (FIG. 2c). These results further support that the nanoparticles obtained in Example 1 possess an anticancer effect.

EXAMPLE 3

Proteomics Profiling of Nanoparticles Secreted from Macrophages

In order to test whether the total amount of the nanoparticles secreted in Example 1-1 was increased according to the introduction of glucose-deprived stress, RAW264.7 cells were stained with DiI (lipophilic fluorescence tracer). After the dye was washed off, the cells were cultured in both the glucose-containing condition and the glucose-deprive condition, respectively. After the particles secreted by the same method as in Example 1 were purified, the total fluorescence intensity was determined. It was verified that the total fluorescence intensity and the protein content of the secreted particles were enhanced by glucose starvation. These particles were confirmed to contain GRS. When the cells were stained with DiI and DAPI, no difference was observed among the cells cultured under the conditions of the presence or the absence of glucose. This suggests that the difference in the fluorescence intensity of the secreted particles does not result from cell density.

Figure 3A:
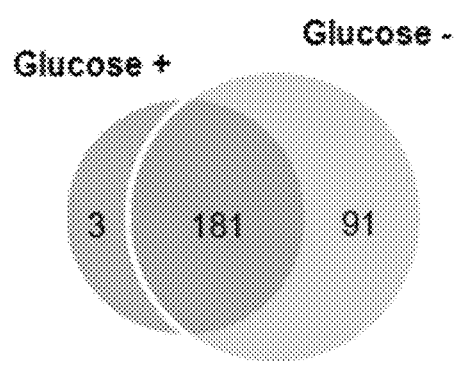
FIG. 3a illustrates the proteomics profile of ARS-SP according to the present invention, showing the numbers of proteins distinctively identified from particles obtained from glucose-containing medium (Glucose +) and glucose-deprived medium (Glucose −) and the relation of sets (red circle: 3, containing glucose; green circle: 91, deficient in glucose).
Figure 3C:
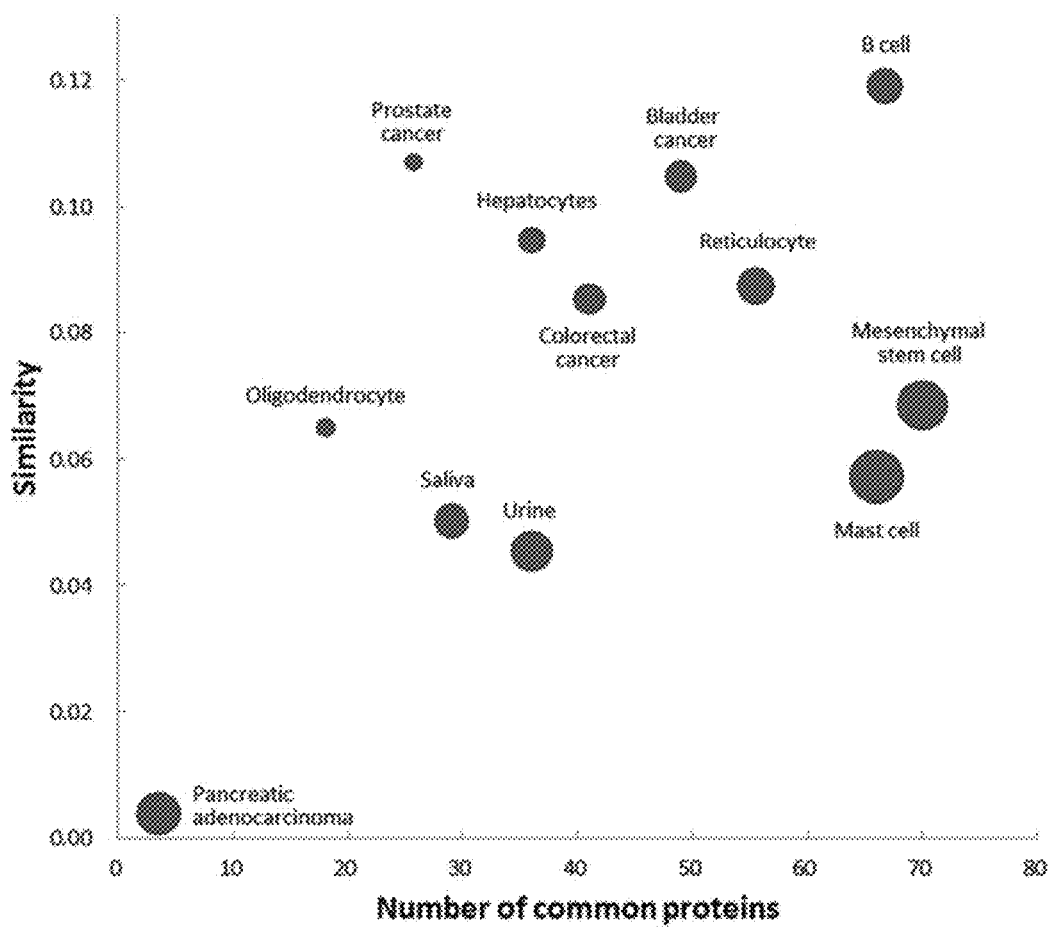
FIG. 3c illustrates comparative results between proteins predominantly identified in ARS-SP and proteins frequently found in exosomes derived from different types of cells.

In order to understand the functions of the nanoparticles obtained in Example 1-1, the protein composition of the nanoparticles was investigated. Macrophages were cultured in the glucose-containing medium (Glucose +) or the glucose-deprived medium (Glucose −). The cell culture media were then collected, centrifuged at 100,000 g to give particles which were then purified by immunoprecipitation using anti-GRS antibodies. The protein components of the particles were separated using SDS-PAGE, while the obtained gel bands were treated with trypsin. The resulting peptides were subjected to LTQ-Orbitrap Velos for LC/MS-MS analysis. Using the MS-GF+ search, 184 and 272 proteins (FDR<0.01) were identified in the particles obtained from glucose-containing and glucose-deprived media, respectively (FIG. 3a). Among the particles obtained in the glucose-deprived condition, 73 proteins were 6-fold increased, while 91 proteins were detected only in the particles obtained from the glucose-deprived condition. These 164 proteins found in the starvation condition were considered as predominant proteins of the nanoparticles of the present invention. Tetraspanin proteins, such as CD9, CD63 and CD82, which are known to be closely associated with exosomes, were not detected in the ARS-SPs according to the present invention (FIG. 3b). When the content of the predominant proteins in the nanoparticles according to the present invention was compared with that of exosomes derived from different cell types listed in Exocarta, a low-degree of similarity could be confirmed (FIG. 3c). These results further support the unique characteristics of the separated nanoparticles according to the present invention.

Upon analyzing predominant proteins of the nanoparticles secreted from the cells cultured in the glucose-deprived condition, leucyl-tRNA synthetase (LRS) and isoleucyl-tRNA synthetase (IRS) as well as glycyl-tRNA synthetase (GRS) were specifically found. All these enzymes are aminoacyl tRNA synthetases, and are involved in protein synthesis. GRS has been known to possess an effect of cancer cell cytotoxicity in addition to that of protein synthesis, while the non-canonical functions of LRS and IRS have been little known. Hereinafter, these nanoparticles will be indicated as ARS-SPs (aminoacyl-tRAN synthetase-secreted particles, or SNAPs).

EXAMPLE 4

Characterization of ARS-SP

Figure 4A:
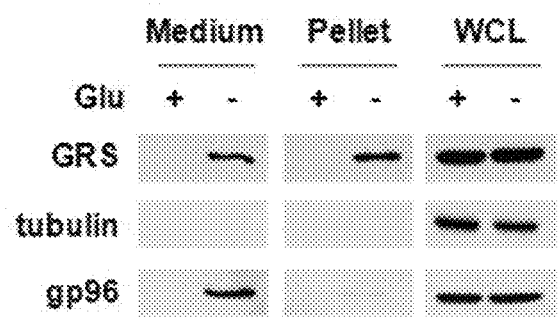
FIG. 4a illustrates immunoblotting results of investigating the presence of GRS and gp96 proteins in the medium obtained after RAW264.7 cells were cultured in the glucose-deprived medium, and in the pellets isolated from the medium, in order to determine characteristics of ARS-SPs isolated and obtained from macrophages cultured in the apoptotic stress environment (glucose-deprived medium) (WCL: whole cell lysate).
Figure 4B:
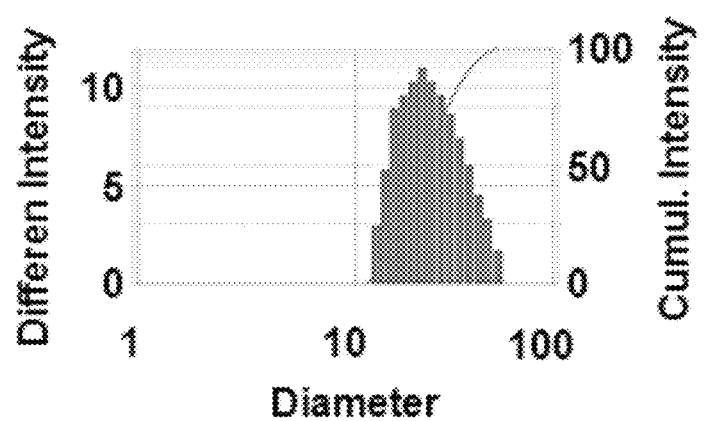
FIG. 4b illustrates the particle size range of ARS-SPs according to the present invention, which are isolated and obtained from macrophages cultured in the glucose-deprived medium, as determined by dynamic light scattering.
Figure 4C:
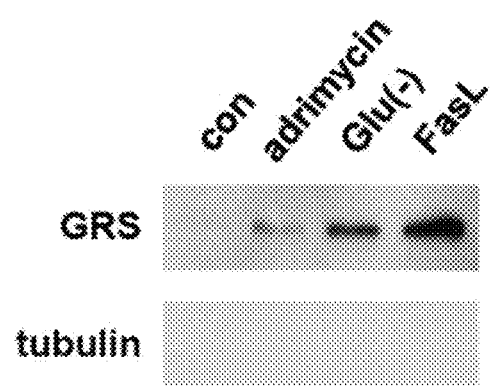
FIG. 4c illustrates results determined by immune-blotting using GRS as a representative marker, whether ARS-SPs according to the present invention were produced in the same manner when apoptotic stresses including adriamycin treatment, glucose-deprived medium, and Fas ligand (FasL) were applied to cells, respectively.
Figure 4D:
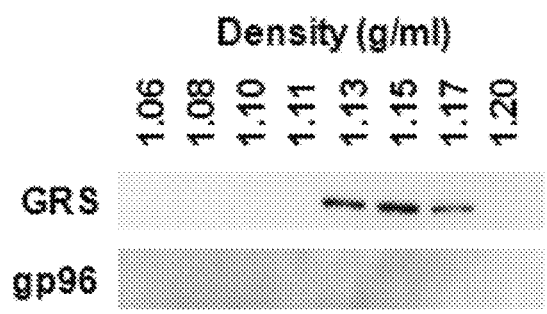
FIG. 4d illustrates results of specific density of ARS-SPs according to the present invention, by analyzing, through immunoblotting, the presence of GRS in each sucrose density gradient fraction when fractionation using sucrose density gradient was performed on pellets from the medium obtained after macrophages were cultured in the glucose-deprived medium.
Figure 4E:
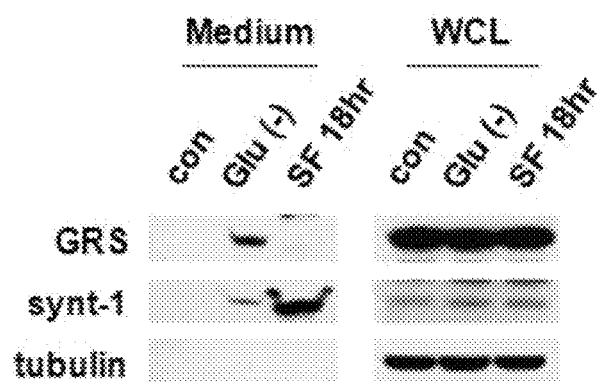
FIG. 4e illustrates immunoblotting results of the presence of exosome marker, syntenin-1, in the medium obtained after macrophages were cultured in the glucose-deprived medium for 4 hr (Glu (−)) or cultured in the serum-free condition for 18 hr (SF 18 hr) (con: glucose-containing media, WCL: whole cell lysate).

In order to analyze characteristics of ARS-SP, RAW264.7 cells were cultured in glucose-containing and glucose-deprived media, respectively. Then, the secreted proteins were fractionated by differential centrifugation. As a result, GRS found in the proteomics profiling in Example 3 was detected in the pellets obtained by centrifugation at 100,000 g (FIG. 4a). The obtained pellets by centrifugation did not contain Gp96 proteins, which are known to be secreted via the ER-Golgi pathway (FIG. 4a). The GRS was detected in the pellets obtained by the same method as described above together with the application of the apoptotic stress (such as adriamycin and FasL) upon the cells, like in the pellets obtained from the glucose-deprived medium (FIG. 4c). Upon measuring ARS-SPs using the light scattering spectrophotometer and analytical gradient ultracentrifugation, it was found that the ARS-SP particles have a mean diameter of 36.9 nm (FIG. 4b) and a buoyant density of 1.13-1.17 g/ml (FIG. 4d). In order to investigate whether the ARS-SPs are distinguishable from exosomes, after RAW264.7 cells were cultured in the glucose-deprived condition and the serum-deprived condition for 4 hr or 18 hr, respectively, syntenin-1, a known exosome marker, and GRS (as contained in the ARS-SP), were measured. As a result, it was confirmed that GRS was secreted from the cells only in the glucose-deprived condition, whereas syntenin-1 was secreted only in the serum-deprived condition (FIG. 4e). These results suggest that the secretion conditions of the proteins including GRS as contained in the ARS-SP, are different from those of exosomes.

Figure 4F:
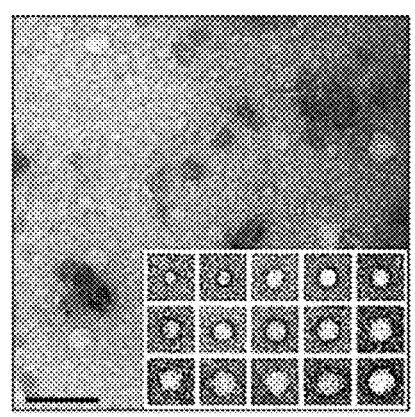
FIG. 4f illustrates electron microscopic results of the morphology of ARS-SP particles, after ARS-SP fractions from the medium obtained by the culture of macrophages in the glucose-deprived medium were negative-stained.
Figure 4G:
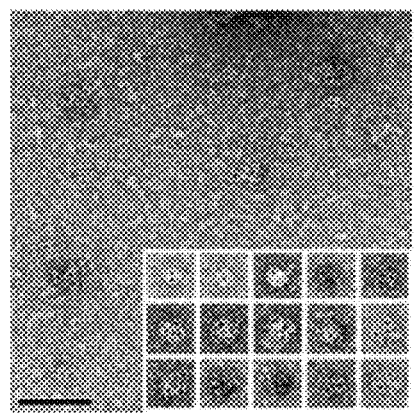
FIG. 4g illustrates results of the localization of GRS, determined by immune-gold labeling of GRS using anti-GRS antibody conjugated with gold particles when ARS-SP fractions from the medium obtained after the culture of macrophages in the glucose-deprived medium were observed through negative staining and electron microscopy (scale bar: 100 nm).
Figure 4H:
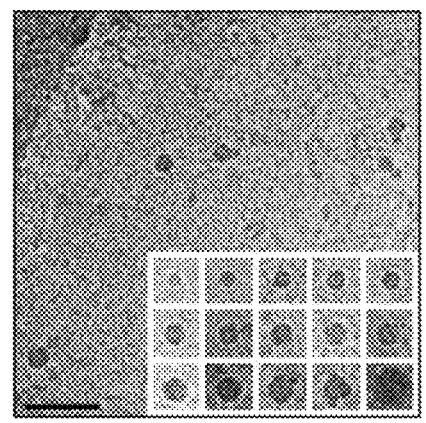
FIG. 4h illustrates the results of the morphology of ARS-SP particles by observing ARS-SP fractions from the medium obtained after the culture of macrophages in the glucose-deprived medium, using cryo-electron microscopy.

The size and morphology of the ARS-SP of the present invention were analyzed by electron microscopy. The negative staining electron microscopy showed that the ARS-SPs have a globular shape and a varying size of 20 to 50 nm (FIG. 4f). In order to investigate whether GRS is present in the nanoparticles, the nanoparticles were stained with gold particle-conjugated anti-GRS antibodies, revealing that the antibodies were enriched on the surface of the 20-50 nm particles (FIG. 4g). Upon further monitoring of the morphology and the size of ARS-SPs using cryo-electron microscopy, the same results as above were obtained (FIG. 4h). The morphology and size of the ARS-SP are distinct from those of exosomes, while showing an apparent similarity to typical lipoprotein particles.

It can be seen from the above results that the ARS-SPs secreted by the apoptotic stress are lipoprotein-like particles, having a diameter of 20-50 nm and a density of 1.13-1.17 g/ml.

EXAMPLE 5

Analysis of Modification of GRS in ARS-SP

Figure 5A:
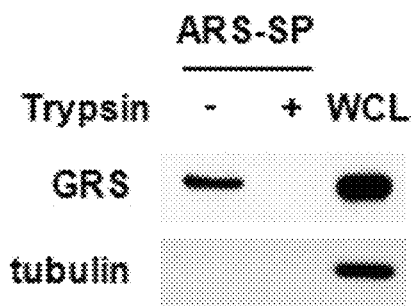
FIG. 5a illustrates the results of the presence of GRS proteins after ARS-SPs were treated with and without trypsin, in older to investigate whether GRS was exposed to the surface of ARS-SP nanoparticles (WCL: whole cell lysate).
Figure 5B:
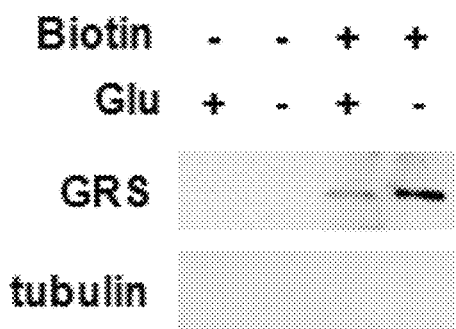
FIG. 5b illustrates results of the presence (localization) of GRS by the biotinylation of ARS-SP and the immunoprecipitation using streptavidin-agarose beads, in order to investigate the localization of GRS in ARS-SP according to the present invention (Glu: glucose-deprived (−) medium or glucose-containing (+) medium condition).

The immunogold labeling of GRS shown in electron microscopy (FIG. 4g) suggests that GRS is located on the surface of the ARS-SP. In order to further confirm this possibility, the ARS-SPs were cultured with trypsin to determine whether GRS was sensitive to protease attack. As a test result, it was confirmed that GRS was removed by the treatment of trypsin (FIG. 5a). Then, in order to label surface proteins of the ARS-SP, the ARS-SPs were biotinylated by using membrane-impermeable biotins, followed by treating the biotinylated ARS-SPs with surfactants and precipitating the biotin-labeled proteins with streptavidin-agarose beads. Then, immunoblotting using anti-GRS antibodies was conducted for analysis. The amount of biotinylated GRSs in the nanoparticles obtained from the glucose-deprived media was increased (FIG. 5b). These results further support that GRS was located on the surface of the ARS-SP.

Figure 5C:
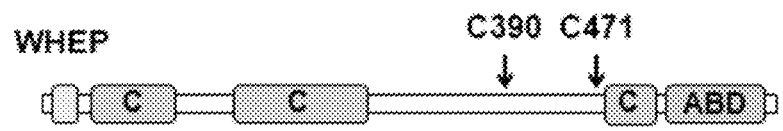
FIG. 5c is a schematic diagram of functional domains of GRS (WHEP, C: catalytic domain, and ABD: anticodon binding domain), indicating the locations of cysteine residues ($390^{th}$ cysteine and $471^{st}$ cysteine) which are predicted to be important in the palmitoylation of GRS.
Figure 5D:
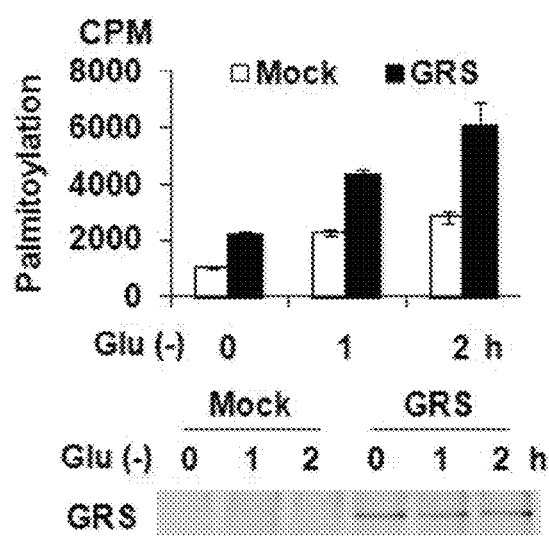
FIG. 5d illustrates the results investigating whether palmitoylation was involved in the secretion of GRS, using the modified metabolic labeling method.
Figure 5E:
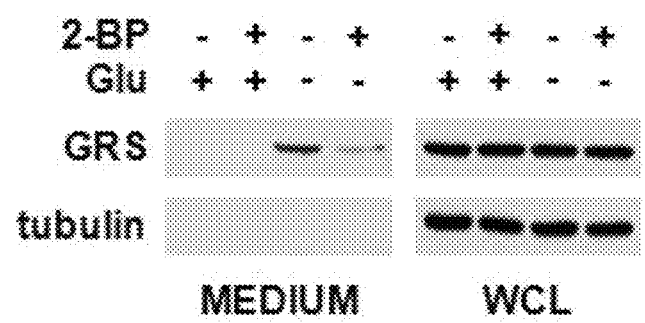
FIG. 5e illustrates the results showing the effect of 2-bromo-palmitate (2-BP) on the secretion of GRS after cells were treated with a palmitoylation inhibitor 2-BP in order to test whether palmitoylation is necessary for GRS secretion (Glu: glucose-deprived (−) medium or glucose-containing (+) medium condition, WCL: whole cell lysate).
Figure 5F:
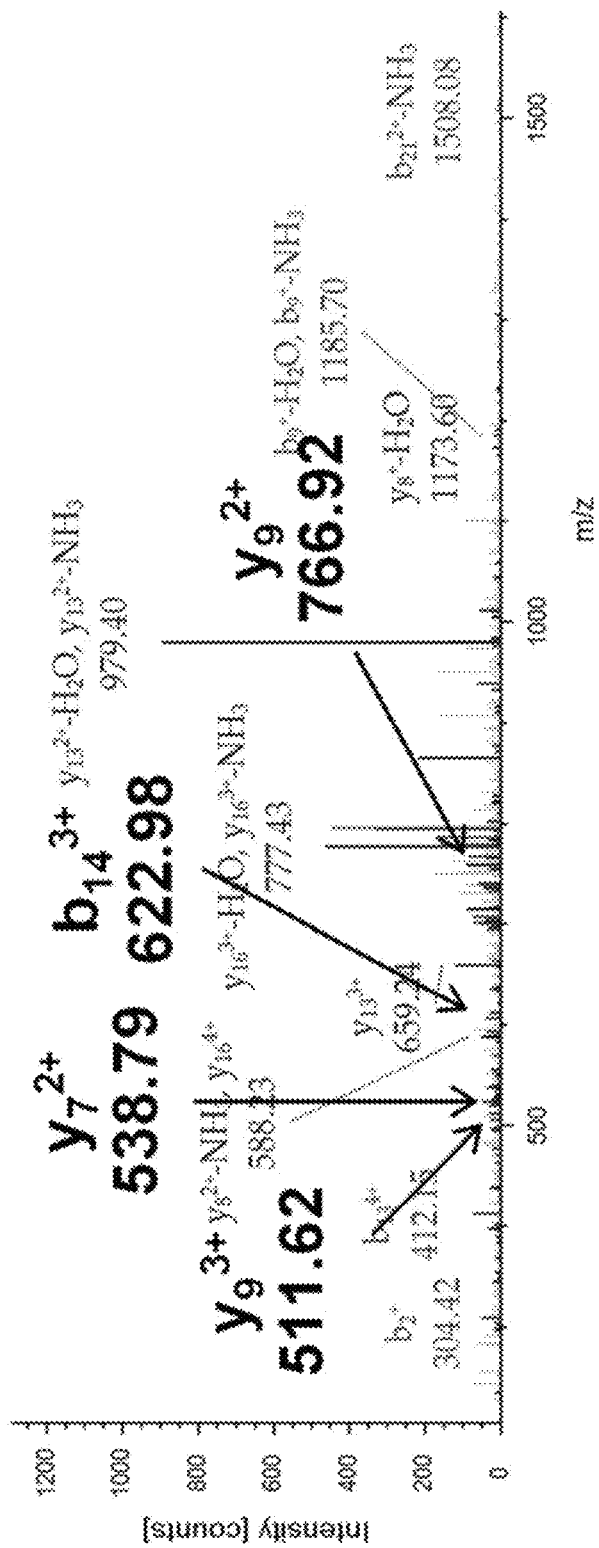
FIG. 5f illustrates LC-MS/MS assay results for the determination of palmitoylation sites in GRS and the sites of palmitoylation determined therefrom.
Figure 5G:
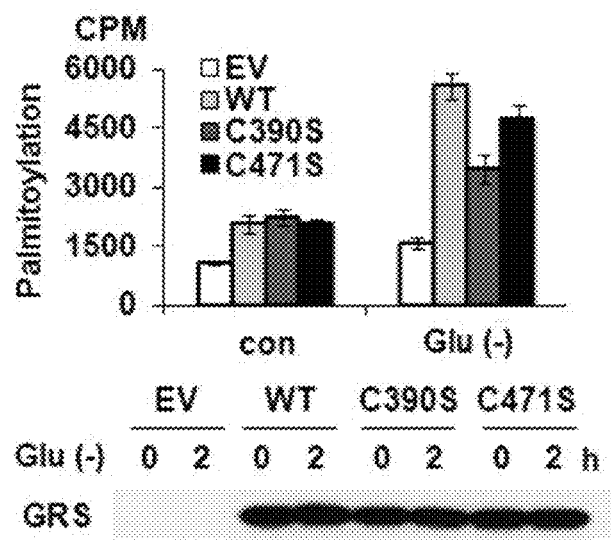
FIG. 5g illustrates the results investigating the attachment of palmitic acid and the secretion through ARS-SP according to the present invention in C390S and C471S mutants of GRS (EV: empty vector, WT: GRS wild type).
Figure 5H:
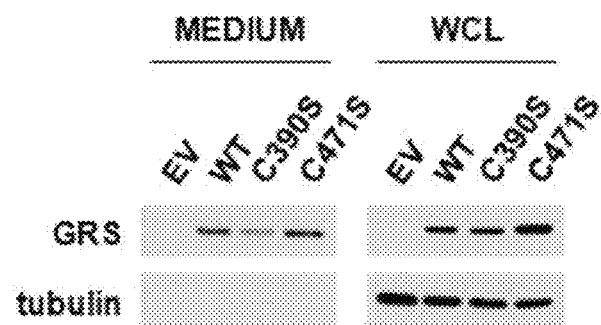
FIG. 5h illustrates the results investigating the secretion degree of ARS-SP according to the present invention in C390S and C471S mutants of GRS, where GRS was used as a representative marker in order to investigate the secretion of ARS-SP (EV: empty vector, WT: GRS wild type).

Molecular mechanisms in which GRS is anchored to the surface of the ARS-SP were investigated. It is expected that GRS has no transmembrane domain, resulting from a sequence analysis using TMHMM server (http://www.cbs.dtu.dk/services/TMHMM, data not shown). The possibility that GRS is anchored to the surface membrane by its lipid modification was tested by analyzing its sequence with CSS-Palm 4.0 software. Two potential sites of palmitoylation were found at C390 and C471 (FIG. 5c). Palmitoylation is known to be reversible and involved with membrane trafficking of cytosolic proteins. In order to determine whether palmitoylation is involved in the secretion of GRS, a modified metabolic labeling method was used. RAW264.7 cells were cultured in glucose-deprived medium with [$^3$H]-palmitic acid, while GRS was immunoprecipitated using anti-GRS antibodies. Interestingly, the palmitoylation of endogenous GRS was increased with glucose starvation (FIG. 5d). In order to confirm whether the palmitoylation is required for GRS secretion, as a result of treating the cells with a palmitoylation inhibitor, 2-bromo-palmitate (2-BP), it was verified that such a treatment inhibited the secretion of GRS (FIG. 5e). Using LC-MS/MS, the palmitoylation sites of GRS were determined to be C390 and a few additional cysteines, excluding C471 (FIG. 5f). This result further supports C390 as a potential real candidate site. In order to validate these results, there were prepared two mutated, tagged forms of GRS (C390S and C471S), of which two cysteine residues C390 and C471 were replaced with a serine residue, respectively. In order to investigate whether these substitutions affect the attachment of palmitic acid and the secretion of GRS, RAW264.7 cells were transfected with the strep-tagged GRS WT and mutant constructs (C390 and C471 mutants) and cultured in glucose-deprived medium (FIGS. 5g and 5h). It was found that both the palmitoylation and the secretion or GRS were reduced in the C390S mutant, in comparison with WT GRS and the C471S mutant.

EXAMPLE 6

Analysis of ARS-SP Secretion Pathway

As described in Example 4 above, it was found that the ARS-SP nanoparticles according to the present invention were secreted in conditions different from those of exosome secretion and were lipoprotein-like particles in view of their morphological characteristics. For further confirmation, the characteristics associated with the secretory pathway of the ARS-SP were investigated.

Figure 6A:
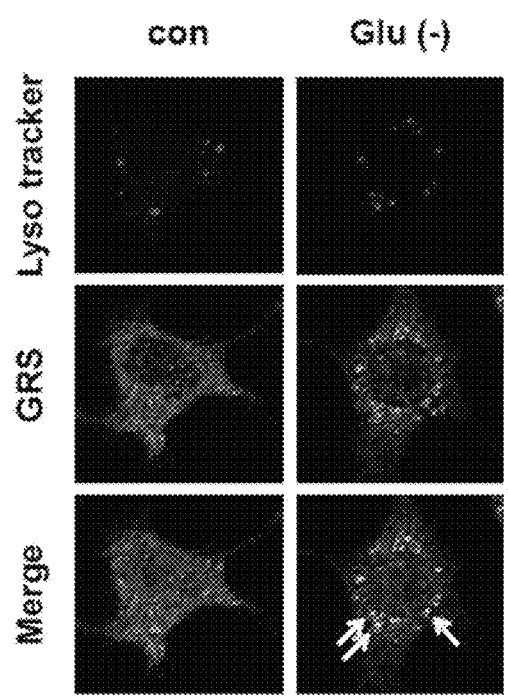
FIG. 6a shows the analysis results of co-localization of GRS with Lysosome tracker.
Figure 6B:
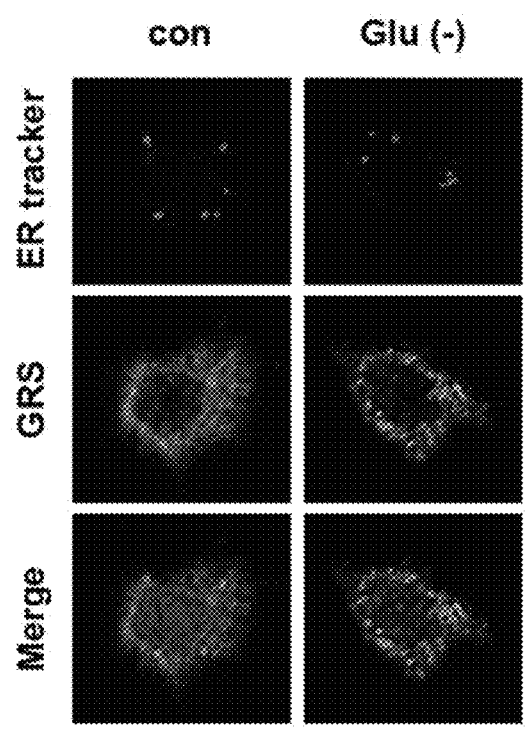
FIG. 6b shows the analysis results of co-localization of GRS with ER tracker.
Figure 6C:
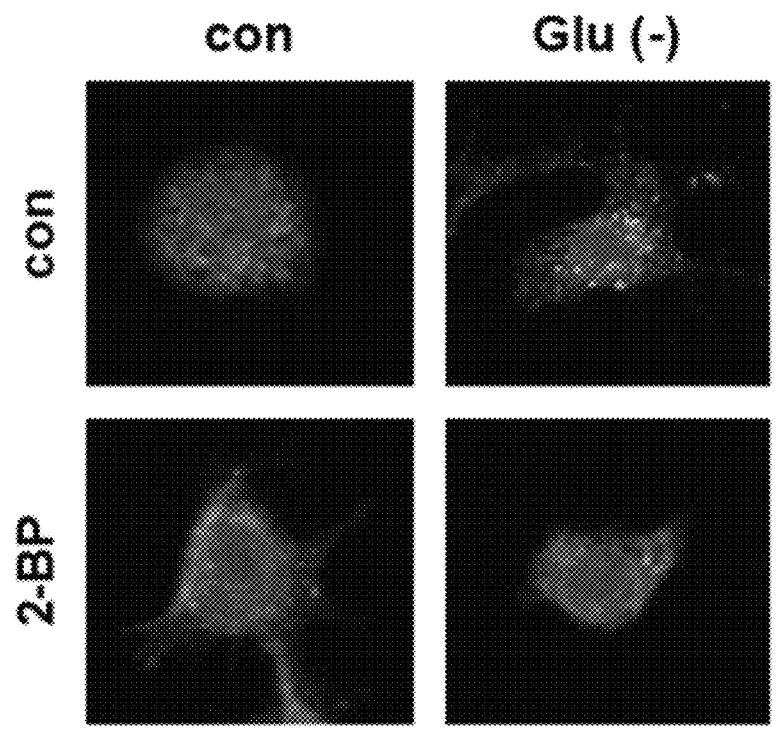
FIG. 6c shows the immunofluorescence staining results of the intracellular GRS-foci formation according to the treatment of cells with a palmitoylation inhibitor, 2-bromo-palmitate (2-BP) (anti-GRS antibody (green) and DAPI (blue)).

In order to investigate the cellular location at which GRS is recruited prior to the secretion of ARS-SPs, intracellular GRS in RAW264.7 cells was visualized using correlative light and cryo-electron microscopy technology, while anti-GRS antibodies conjugated to Alexa488 fluorescent dye were used for immunolabeling. Using confocal fluorescence microscopy, the fluorescence-labeled regions were first identified, and then cryo-fixation and electron microscopic observation were performed. Out of the obtained images, the fluorescence-labeled regions (white boxes in each panel) were found. The fluorescence-labeled regions contain globular-shaped particles as consistent with the result of the cryo-EM morphology shown in FIG. 4h, without the presence of MVB. This observation results demonstrated distinctive characteristics of GRS particles in terms of its size and cytosolic localization, in comparison with the fact that exosomes have a large size and co-exist with MVB upon being cultured in the glucose-deprived condition for 2 hr. Interestingly, it was found that glucose starvation increased the formation of cytosolic foci of GRS. When the co-localization analysis of GRS was performed with lysosome and ER trackers, it was verified that the GRS foci were not perfectly superimposed with either of the two markers (FIGS. 6a and 6b). Then, it was tested whether the palmitoylation of GRS was associated with its intracellular localization, revealing that the glucose starvation-induced GRS foci were inhibited by the treatment of 2-BP (FIG. 6c). These facts suggest that the lipid modification is necessary for the recruitment of GRS to the secretory particles in the cytosol prior to its secretion, which is different from the generally known secretory pathway of exosomes.

EXAMPLE 7

Verification on Anticancer Activity Cofactor of ARS-SP

Figure 7A:
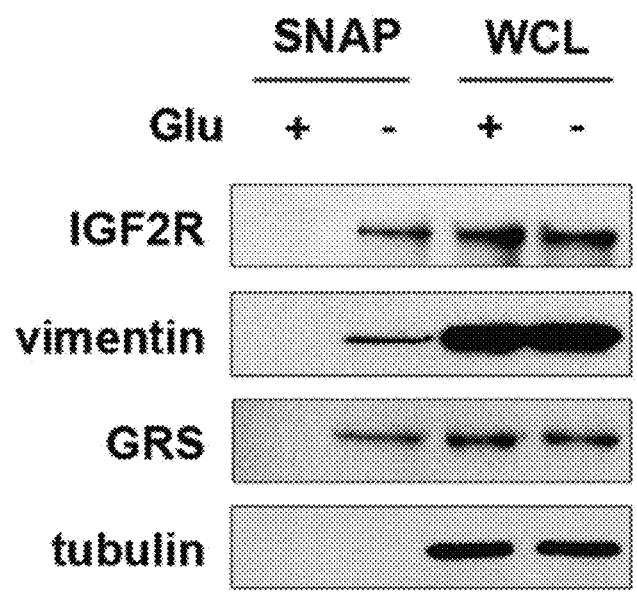
FIG. 7a illustrates the immunoblotting results of the presence of IGF2R and vimentin in ARS-SP according to the present invention (indicated as SNAP) (WCL: whole cell lysate).
Figure 7B:
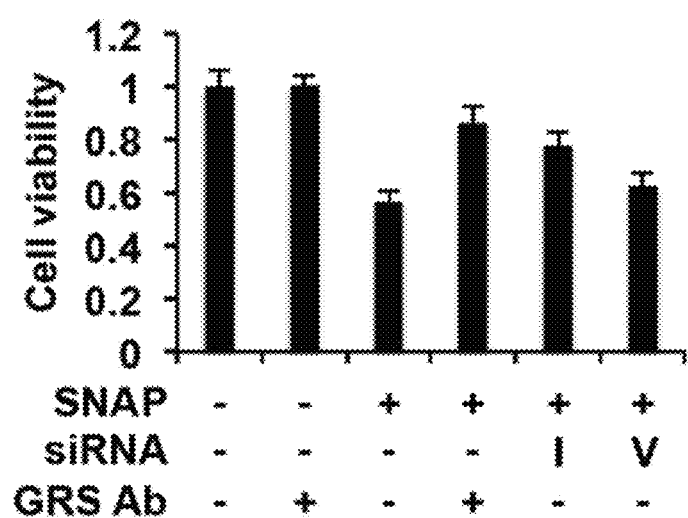
FIG. 7b illustrates the results of the effect of ARS-SP according to the present invention (indicated as SNAP) on cancer cell viability when the ARS-SPs were isolated after the expressions of IGF2R and vimentin were inhibited using siRNA specific thereto (Among the siRNA treatments, I means si-IGF2R treatment and V means si-vimentin treatment; GRS Ab means treatment of cells with anti-GRS antibody).

The possibility that the ARS-SP may contain additional apoptotic factors was investigated by a method for selectively depleting some components in the secreted particles. Among factors identified in the ARS-SP, the investigation was focused on factors involved in the apoptotic processes such as IGF2R and vimentin. The presence of such factors in the separated ARS-SP was confirmed by western blotting using antibodies specific thereto (FIG. 7a). Then, the expression of the respective factors (IGF2R and vimentin) was inhibited in macrophages RAW264.7 by using siRNAs specific thereto, while the nanoparticles were manufactured by the same method as described in Example 1-1. Cancer cells were treated with the prepared IGF2R-removed or vimentin-removed ARS-SPs as such, followed by the comparison of their cancer apoptotic activities. Compared with the prepared ARS-SPs secreted from normal macrophages, the ARS-SP nanoparticles prepared from the cells having an inhibited expressions of IGF2R or vimentin showed a reduction in their apoptotic activity. This result suggests that, in addition to GRS, IGF2R and vimentin also partially contribute to the anticancer activity of the ARS-SP according to the present invention (FIG. 7b).

EXAMPLE 8

Molecular Mechanisms of ARS-SP Action on Cancer Cells

Figure 8A:
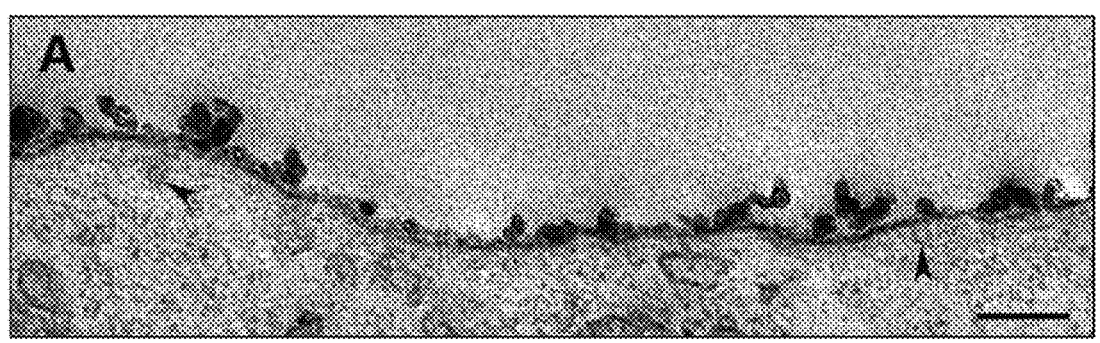
FIG. 8a shows an electron microscopic image of cancer cells (H460) which were treated with ARS-SPs according to the present invention and, after 10 min, chemically fixed. The images display the plasma membrane with its intra- and extracellular regions, while black arrowheads point ARS-SPs (scale bar=200 nm).
Figure 8B:
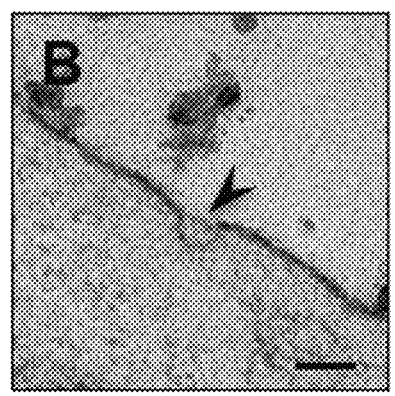
FIG. 8b shows an electron microscopic image of cancer cells (H460) that were treated with ARS-SPs according to the present invention and, after 10 min, chemically fixed. The images display the plasma membrane with its intra- and extracellular regions, while the black arrowhead points ARS-SP (scale bars=100 nm).
Figure 8C:
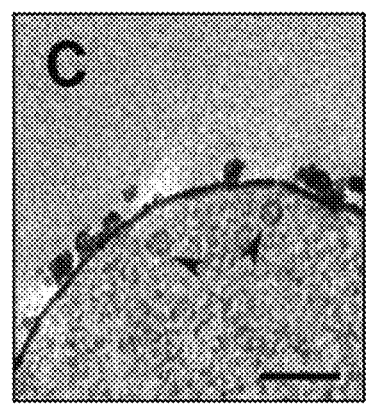
FIG. 8c shows an electron microscopic image of cancer cells (H460) that were treated with ARS-SPs according to the present invention and, after 10 min, chemically fixed. The images display the plasma membrane with its intra- and extracellular regions, while black arrowheads point ARS-SP (scale bar=200 nm).
Figure 8D:
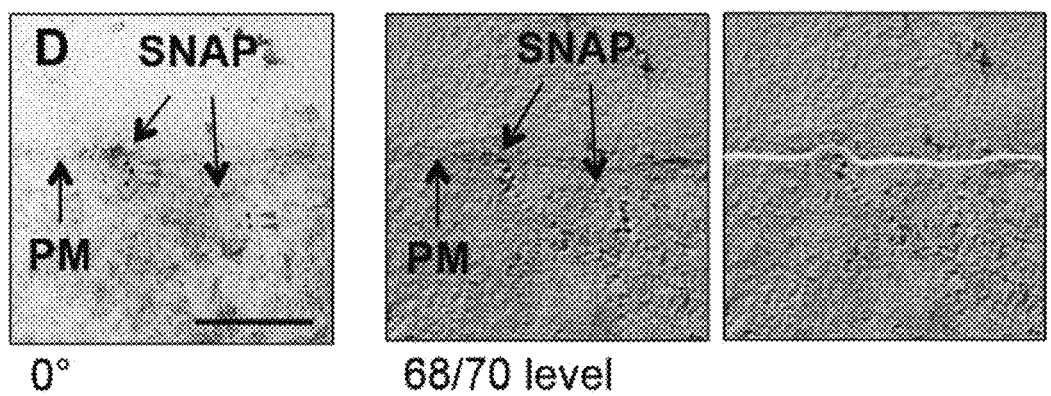
FIG. 8d illustrates the results of cryo-fixation electron microscopy of immuno-gold labeled ARS-SPs absorbed by cancer cells (H460), indicating that endocytosed ARS-SPs actually contain GRS. ARS-SP-treated H460 cells were cryo-fixed and immuno-stained with anti-GRS antibody. For tomography, proper images of each sample were recorded over by increasing the angle range from −60° to +60° by 2°. Each numerical value means the angle of the proper sample (left). The proper images were aligned, and then used for constructing tomograms. Each numerical value indicates the order of tomographic slices (middle). The plasma membrane and ARS-SPs were shown by yellow and blue lines, respectively (right). Scale bar=100 nm, PM: plasma membrane.
Figure 8E:
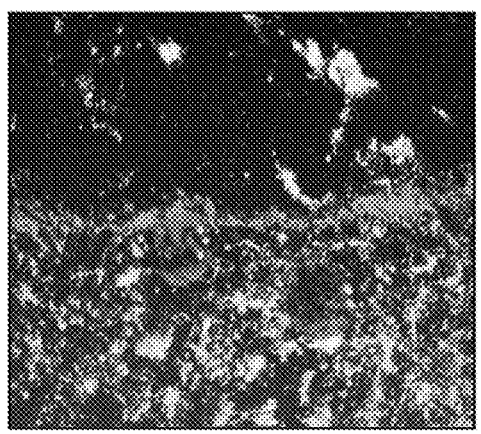
FIG. 8e illustrates the results of 3D electron tomography of immuno-gold labeled ARS-SPs absorbed by cancer cells (H460), indicating that endocytosed ARS-SPs actually contain GRS.

In order to understand the action mechanism of the ARS-SPs according to the present invention on cancer cells, a test was conducted using a cancer cell line H460. First, the uptake of ARS-SPs into the H460 cells was monitored (observed) by using electron microscopy. The H460 cells were treated with the ARS-SPs. After 10 min, it was observed (detected) that a large amount of the ARS-SPs were anchored to the cellular membrane surface of the cancer cells (FIG. 8a). Furthermore, it was detected that the ARS-SPs were in different stages of endocytosis (FIGS. 8b and 8c). Following immunogold-labeling of GRS, cryo-fixation electron microscopy and 3D electron tomography were performed, demonstrating that the endocytosed ARS-SPs actually contained GRS as described above (FIGS. 8d and 8e).

EXAMPLE 9

ARS-SP Separation by Co-Culture with Cancer Cells

Figure 8F:
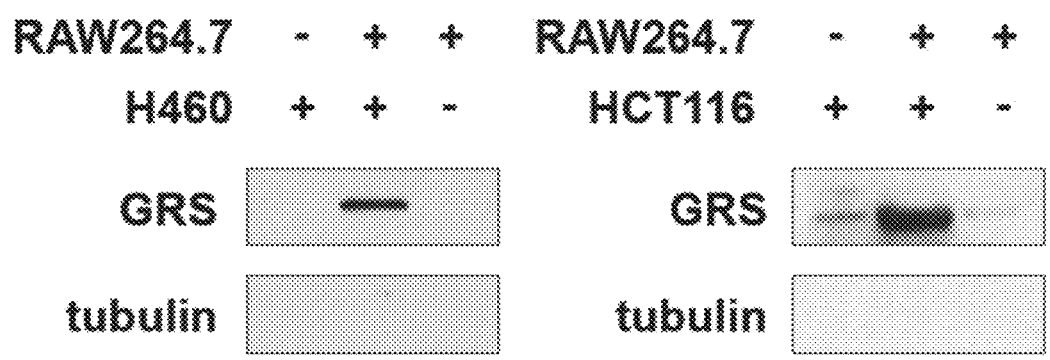
FIG. 8f illustrates the results of the secretion of ARS-SP from macrophages by cancer cell challenge.

In order to investigate whether the secretion of the ARS-SPs according to the present invention can be induced by cancer cell change, macrophages (RAW264.7) and cancer cells (H460 or HCT116) were co-cultured, confirming the secretion of ARS-SPs by using the presence of GRS as a marker. In order to prevent the physical interaction between macrophages and cancer cells, cancer cells and macrophages were seeded in upper and lower chambers of the 0.4 mm pore-size transwell plates, followed by culture in serum-deficient DMEM media overnight. GRS was detected in the nanoparticles from the cell culture medium in the upper chamber, which was separated in the same method as Example 1-1 (FIG. 8f), which suggests that the ARS-SPs are secreted even through the co-culture with cancer cells.

In addition, the present inventors co-cultured human monocytes U937 cells and lung cancer cells H460 cells in serum-deficient RPMI medium. The culture medium was separated and then centrifuged three times at 500 g (15 min), 10,000 g (15 min), and 100,000 g (90 min), respectively, to obtain pellets. It was found that the ARS-SPs according to the present invention were present in the pellets.

Figure 8G:
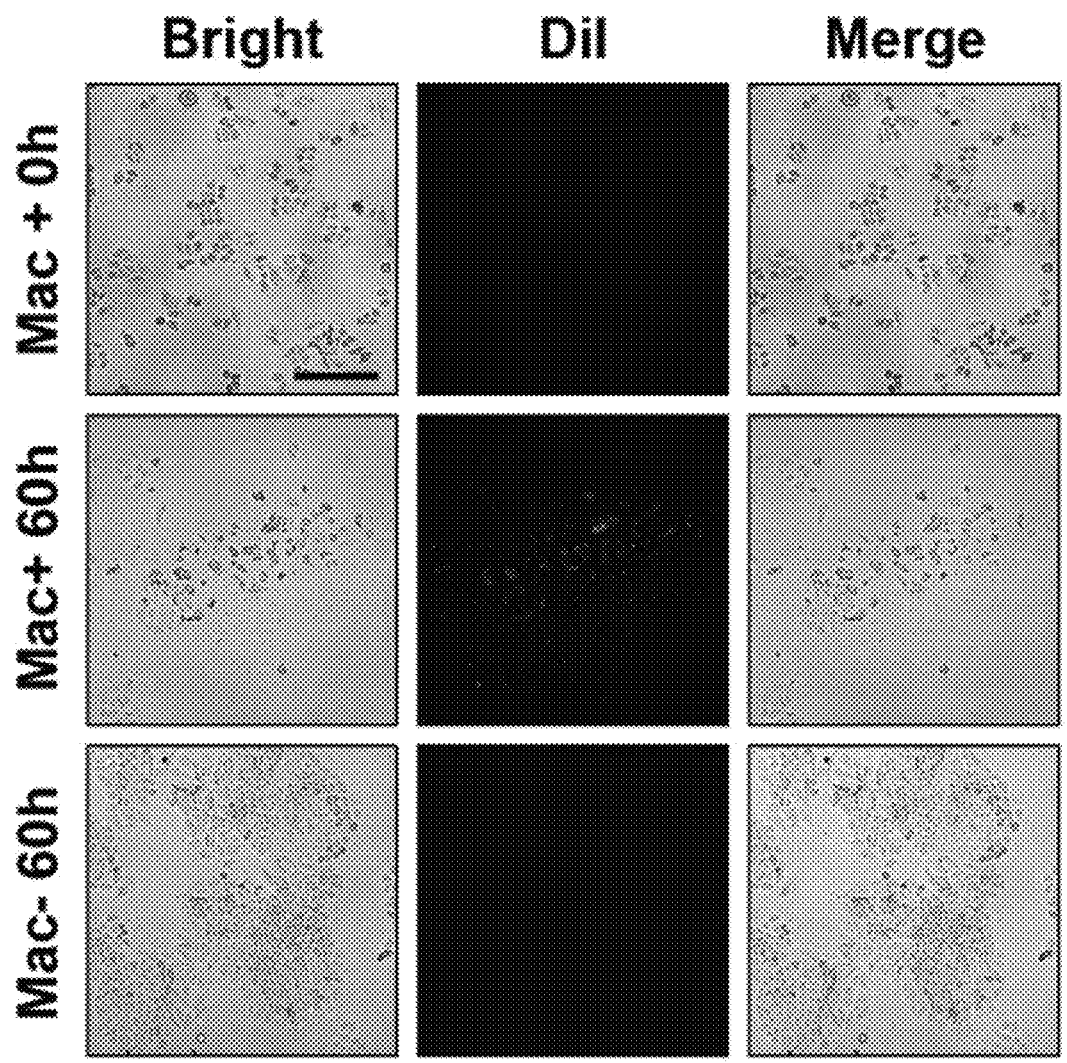
FIG. 8g illustrates the observation results of the passage of ARS-SPs into cancer cells from macrophages, using the transwell chamber. Specifically, DiI-labeled RAW264.7 and H460 cells were seeded in upper and lower chambers of the transwell (0.4 mm pore size), respectively. After co-culturing for 60 min, DiI-labeled ARS-SPs (red) originated from macrophages in the lower chamber and the cell saturation degree (bright region) of cancer cells were observed by a fluorescence microscope (scale bar=50 μm, MAC+: macrophage treatment in the upper chamber, MAC−: macrophage non-treatment in the upper chamber).

In addition, the passage of the ARS-SPs onto cancer cells from macrophages was observed using the transwell chamber. During this test, the macrophages and the cancer cells were cultured, while the macrophages with DiI (red fluorescence dye)-labeled membrane lipids were located in the upper chamber, whereas the cancer cells were located in the lower chamber. Then, the presence of structures labeled with red fluorescence, which exits in the cancer cells, and the effect thereof on the death of the cancer cells were observed. The red fluorescence originating from the macrophages was observed in the cancer cells, and dead cells were detected at the locations of red fluorescence (FIG. 8g).

EXAMPLE 10

Figure 9:
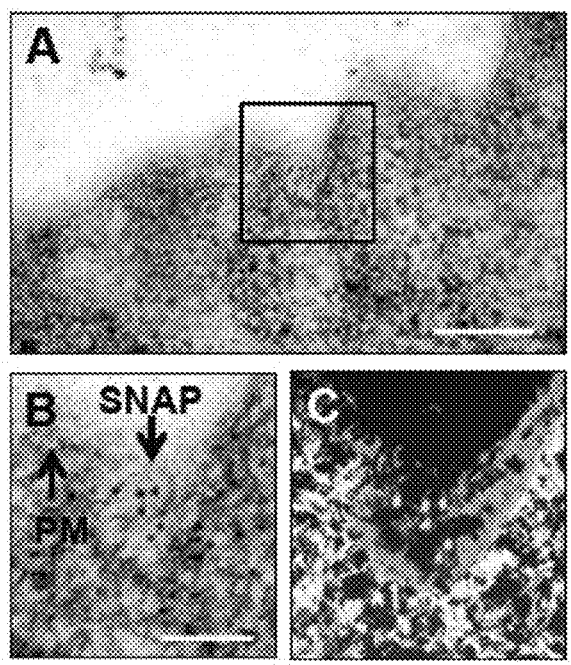
Figure 10A:
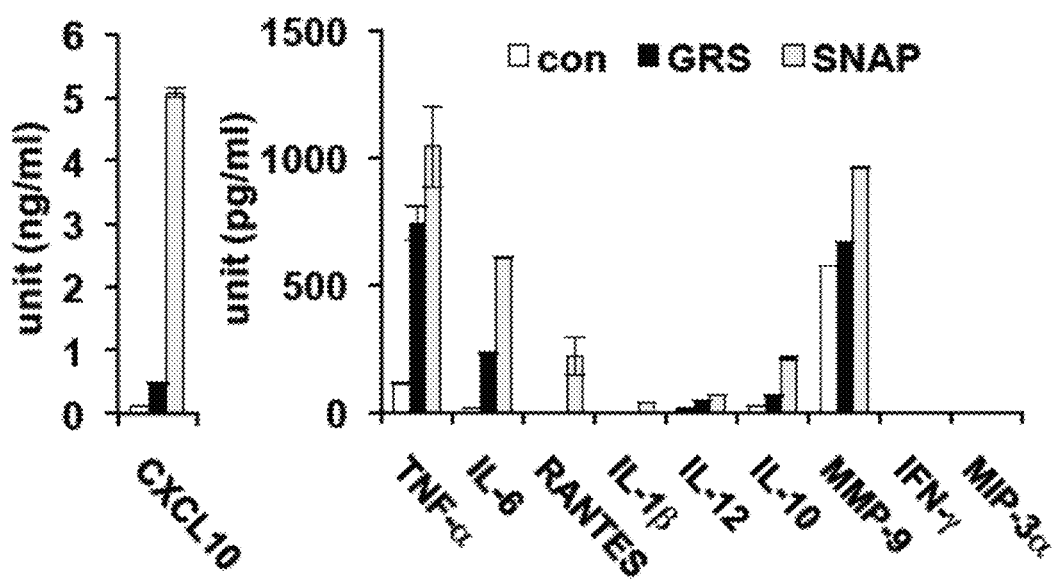
FIG. 10a illustrates the results of cytokine profiles determined by multiplex cytokines assay. RAW264.7 cells were treated with GRS (100 nM) or ARS-SPs (10 mg/ml) for 6 hr. The cell culture media were collected, while secreted cytokines were measured.
Figure 10B:
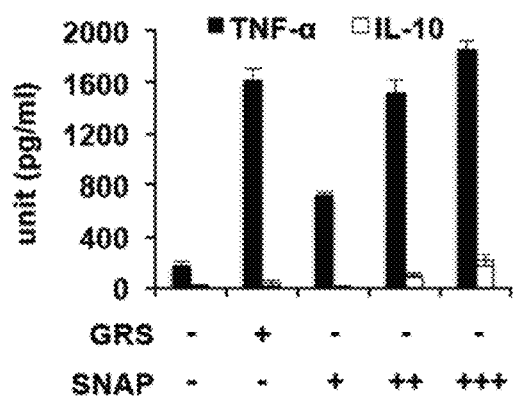
FIG. 10b illustrates the ELISA results of the concentration-dependent effect of ARS-SP (SNAP) on the secretion of TNF-α and IL-10.
Figure 10C:
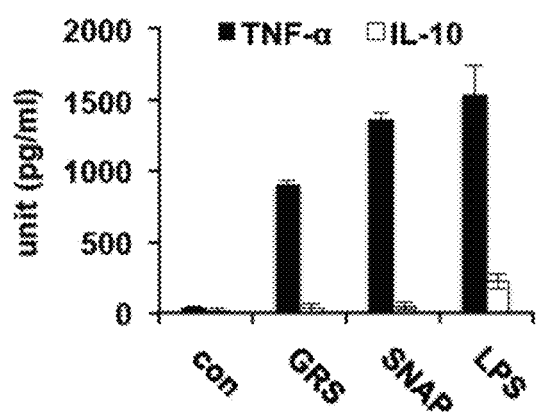
FIG. 10c illustrates the results of the secretion of TNF-α induced by the treatment of ARS-SPs or GRS in the bone marrow-derived macrophage (BMDM). Isolated BMDM cells were cultured together with ARS-SPs or GRS for 6 hr. The secretion of TNF-α and IL-10 was determined by ELISA (LPS: lipopolysaccharide-treated positive control).
Figure 10D:
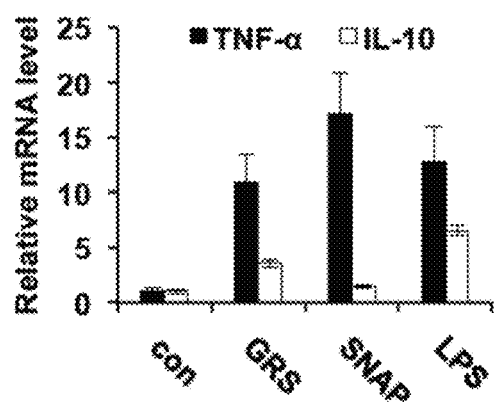
FIG. 10d illustrates the qRT-PCR analysis results of the expression levels of transcripts of TNF-α and IL-10 (M1 markers) in BMDM treated with ARS-SPs or GRS for 4 hr (LPS: lipopolysaccharide-treated positive control).
Figure 10E:
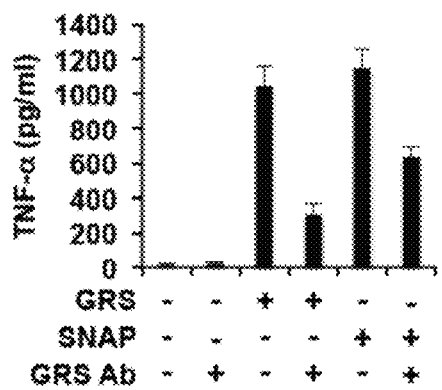
FIG. 10e illustrates the ELISA results of TNF-α secreted in the culture medium after macrophages were treated with ARS-SPs (SNAPs) or GRS which were pre-incubated with anti-GRS antibody for 30 min.
Figure 10F:
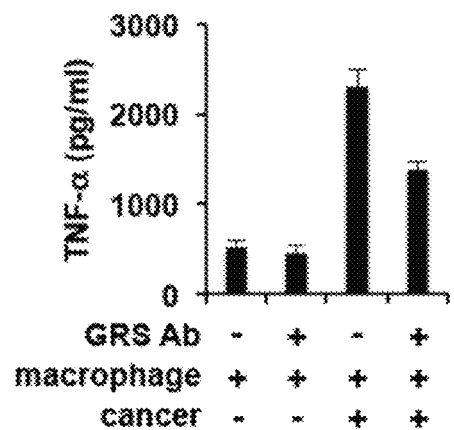
FIG. 10f illustrates the ELISA results of the secretion of TNF-α after macrophages (RAW264.7) and cancer cells (H460) were co-cultured. In order to investigate the effect of GRS in the co-cultured samples, anti-GRS antibody was added to the co-cultured medium.
Figure 10G:
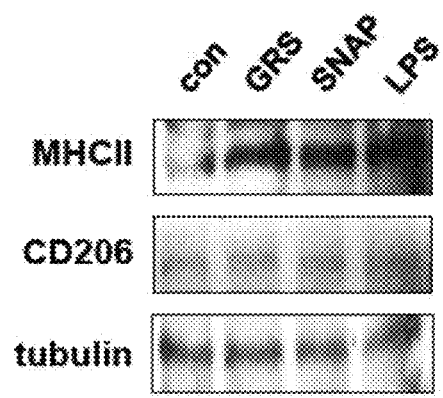
FIG. 10g illustrates the immunoblotting results of MHCII, which is the M1 polarization marker protein, and CD206, which is the M2 polarization marker protein, after RAW264.7 cells were cultured together with ARS-SPs or GRS for 12 hr (LPS: lipopolysaccharide treated positive control).
Figure 10H:
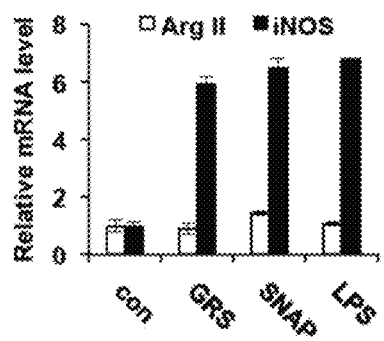
FIG. 10h illustrates the qRT-PCR analysis results of the expression levels of transcripts of iNOS and Arginase II (M2 markers) in BMDM treated with ARS-SPs or GRS for 4 hr. Error bar indicates mean±standard deviation from average three times of repeated tests (LPS: lipopolysaccharide treated positive control).

The Effect of ARS-SP in Enhancing Immune Function
<10-1> Verification on the In Vitro Effect of ARS-SP in Enhancing Immune Function It was investigated whether the ARS-SP according to the present invention had an autocrine effect on macrophages. It was verified through immune-gold staining and 3D tomography of GRS that the ARS-SP nanoparticles were taken up into macrophages by endocytosis when macrophages were treated with the ARS-SPs (see FIG. 9). Example 1 verified that the ARS-SP does not affect the viability of macrophages. Thus, it was tested whether the ARS-SP affected the differentiation of macrophages. It was found that the ARS-SP as well as GRS increased the production of signature factors of M1-type polarization including TNF-$\alpha$, IL-6, and CXCL10, whereas not increasing M2-type factors including IL-1$\beta$, IL-10, MMP-9, and MIP-3$\alpha$ (FIG. 10a). The particular effects of the ARS-SP in various concentrations on TNF-$\alpha$ induction was further validated (FIG. 10b). In order to further investigate these activities, bone marrow-derived macrophages (BMDD) were treated with the ARS-SPs according to the present invention or GRS, followed by monitoring the induction of TNF-$\alpha$ and IL-10 via ELISA and qRT-PCR. Regarding the above two tests, it was detected that TNF-$\alpha$ was strongly induced in all the test groups, whereas IL-10 was not (FIGS. 10c and 10d). In order to investigate whether GRS is a key factor in the induction of M1 cytokine secretion, the ARS-SPs were pre-incubated with anti-GRS antibodies, followed by the treatment with macrophages. As a result, the secretion of TNF-$\alpha$ induced by the ARS-SP was significantly reduced by anti-GRS-antibodies (up to 50%) (FIG. 10e). When the macrophages were co-cultured with the cancer cells using 0.4 mm pore size transwell plates in the same manner described as above, the secretion of TNF-$\alpha$ was further increased, but was partially reduced by the treatment with anti-GRS antibodies (FIG. 10f). This result further confirmed the importance of GRS in said activity. Further, additional test was conducted to investigate whether ARS-SP could induce MHCII and iNOS, which are other known biomarkers of M1-type macrophages. It was found that the ARS-SP induced MHCII and iNOS like GRS and LPS, whereas it did not exert any effect on CD206 and arginase II which are known as markers of M2 type macrophages (FIGS. 10g and 10h).

Figure 10I:
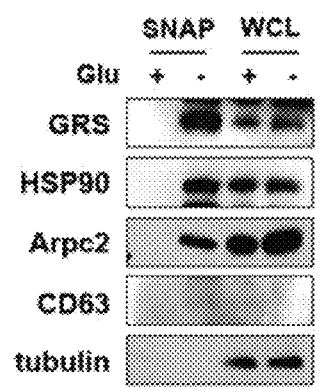
FIG. 10i illustrates the results or the presence of Arpc2, GRS, and HSP90 in ARS-SPs (SNAPs) by immunoblotting using antibodies specific thereto. CD63 (one of exosome markers) was used as negative control (Glu: meaning glucose-deprived (−) medium or glucose-containing (+) medium condition, WCL: whole cell lysate).
Figure 10J:
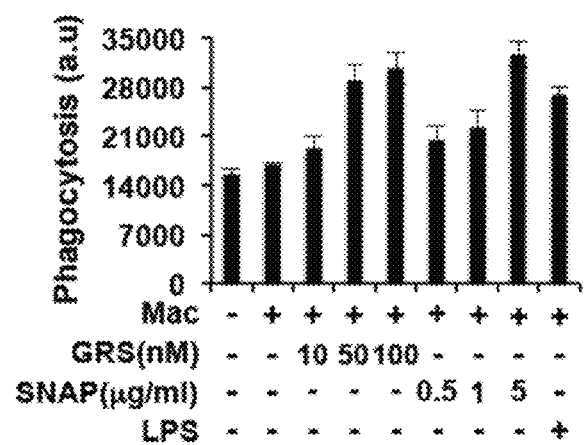
FIG. 10j illustrates the results of the fluorescence intensity by the microplate reader in order to quantify phagocytosis (phagocytic ability) induced by ARS-SP (SNAP) or GRS (Mac: macrophages). Error bar indicates mean±standard deviation from an average of three times of repeated tests.

The phagocytic activity is still another characteristic of M1-type macrophages. The proteomic analysis of the ARS-SP suggests the possible presence of actin-related protein 2/3 complex (Arp2/3 complex) in the ARS-SP. The Arp2/3 complex is known to be related with phagocytosis. Therefore, it was investigated by western blotting whether Arpc2, a key factor of the Arp2/3 complex, was actually present in the ARS-SP. As a result, it was verified that Arpc2 actually existed in the ARS-SP as well as GRS and HSP90, whereas CD63, which is known as an exosome marker, did not exist therein (FIG. 10i). The effect of the ARS-SP on phagocytic activity of macrophages was monitored in tests in which green fluorescence phagocytosis beads was used as a prey. Like LPS, the ARS-SP and GRS improved the phagocytic activity of macrophages in a concentration-dependent manner (FIG. 10j).

Figure 11A:
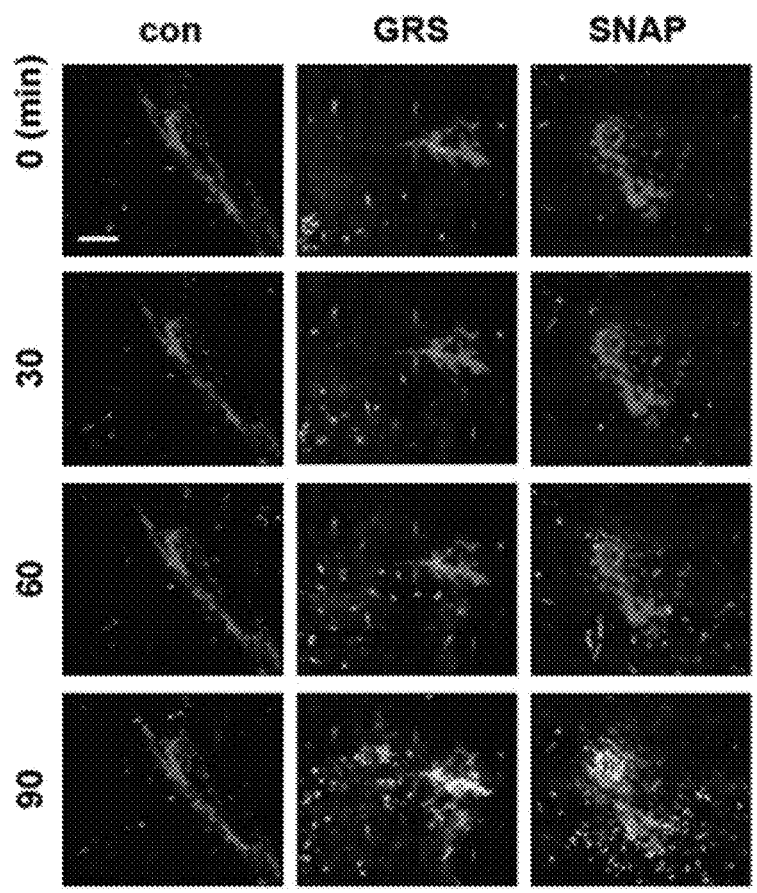
FIG. 11a illustrates the observation results of phagocyte inducing action of ARS-SP in vivo. ARS-SPs (SNAPs) or GRS was intradermally injected into the skin of LyzM-GFP mice. After 6 hr, Alexa594-conjugated bioparticles (red) were injected, and phagocytic activity of macrophages/neutrophils (LyzM, green) was visualized using custom-built, confocal microscopy for 90 min. scale bar=100 nm
Figure 11B:
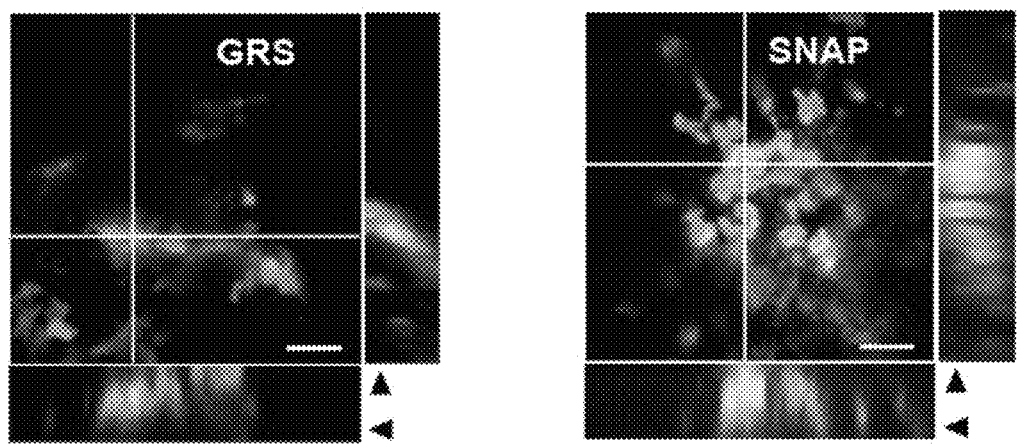
FIG. 11b illustrates the comparison of the Z stack analysis results (left) of the co-localization of GRS-treated macrophages (green) with phagocytic beads (red) and the Z stack analysis results (right) of the co-localization of ARS-SP (SNAP)-treated macrophages (green) with phagocytic beads (red).

<10-2> Verification on the In Vivo Effect of ARS-SP in Enhancing Immune Function The in vivo phagocytosis-stimulating activity of the ARS-SP was further monitored through the intravital monitoring system. LysM-GFP mice were used for the present test, while macrophages/neutrophils in the mice could be monitored by GFP. The ARS-SPs or GRS was first injected into the ear of mice for 6 hr. Then, the red fluorescence-labeled phagocytosis beads were introduced through the same route, while the motion and the phagocytic activity of macrophages were monitored at predetermined time intervals, it was found that the pre-treatment of the ARS-SP or GRS strongly increased the phagocytic activity of macrophages/neutrophils (FIG. 11a), in each test, LPS was used to validate the intravital phagocytosis system. Further, the Z stack analysis identified the accurate locations of macrophages/neutrophils (green) existing together with the beads (FIG. 10b). Therefore, it was verified that the activities of the ARS-SP on cancer cells and macrophages were reproduced in vivo.

EXAMPLE 11

Comparison of Anticancer Activity of ARS-SP

The present inventors found through the above tests that GRS was contained in the ARS-SF according to the present invention, while the GRS proteins as polypeptides per se are known to have an anticancer activity. The present inventors compared the anticancer activity between GRS proteins and the ARS-SP according to the present invention.

<11-1> Comparison of In Vitro Anticancer Activity

H460 cells and RAW 264.7 cells were first treated with GRS or the ARS-SPs by the same method as in Example <1-2> above, followed by determining the viability of those cells. In addition, 15 different types of cancer cell lines (HCT116, SN12C, Caki-1, H1975, HCC44, HCC15, A549, H23, HCC2108, H1703, MCF7, BT-474, RENCA, H1299, and HCC827) were treated with GRS or the ARS-SPs by the same method as in Example <1-2>, followed by comparing their apoptotic activity on those cells.

Figure 12A:
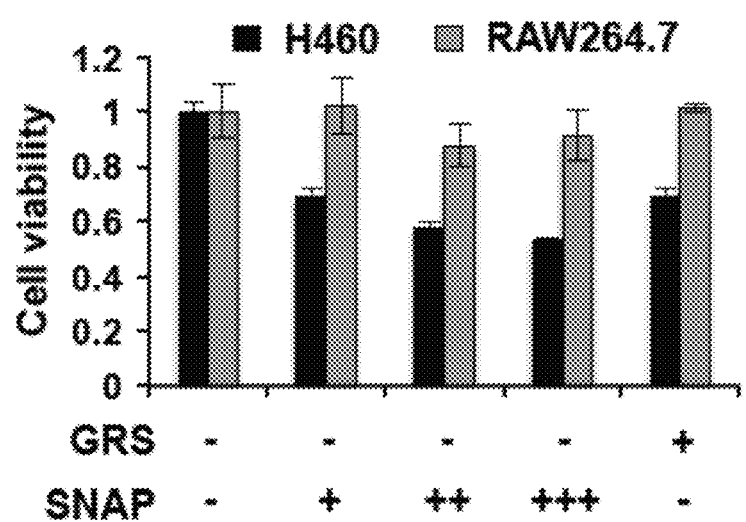
FIG. 12a illustrates the comparison results of cell viability of cancer cells (H460) and macrophages (RAW 264.7) determined by MTT assay when H460 cells and RAW 264.7 cells were treated with ARS-SPs (SNAPs) or GRS for 24 hr (Error bar indicates mean±standard deviation from an average of three times of repeated tests).

As a result, as shown in FIGS. 12a and 12b, considering that the same amounts of the ARS-SP and GRS were used for said tests, the ARS-SP according to the present invention showed a higher cancer apoptotic efficacy than GRS proteins. Especially, as shown in FIG. 12b, the ARS-SP and GRS induced apoptosis in 13 and 9 different cell lines out of a total of 15 cancer cell lines, respectively, suggesting that the ARS-SP acts on a wider spectrum of cancer cells.

<11-2> Comparison of In Vivo Anticancer Activity

Figure 13C:
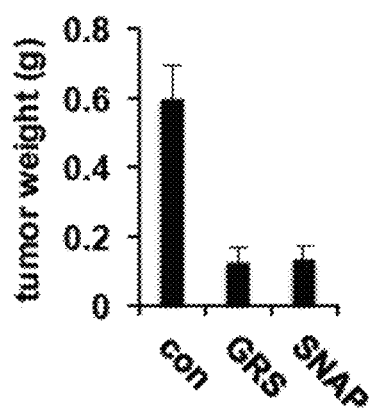
FIG. 13c illustrates the tumor weight measurement results of test groups and the control 15 days after H460 cells ($7.5 \times 10^6$), together with ARS-SPs (SNAPs, 6 mg/kg) or GRS (6 mg/kg) were subcutaneously injected to the flank of BALB/c nude mice (tumor initiation model).

H460 cells were first injected into BALB/c nude mice (tumor initiation models) together with the treatment of the ARS-SP or GRS, and then the effect of such treatment in triggering the occurrence of tumor was monitored. For 15 days, tumors in the control group grew to 100 mm$^3$ or larger, whereas only two out of six animals showed tumors growing to 100 mm$^3$ or more in the ARS-SP or GRS treatment groups (FIG. 13a). The ARS-SP or GRS treatment significantly reduced the tumor volume and weight (FIGS. 13a and 13b), but hardly affected the body weight.

Figure 14A:
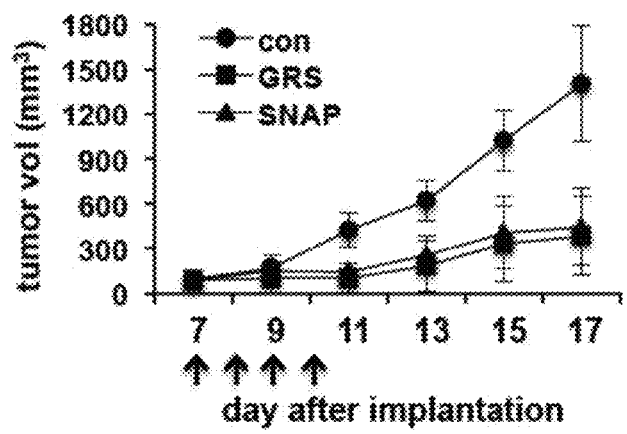
FIG. 14a illustrates the results of tumor growth (volume) in tumor xenograft models. The tumor xenograft models were constructed by subcutaneously injecting H460 cells into nude mice, and on day 7 after tumor implantation, ARS-SPs (SNAPS, 6 mg/kg) or GRS (6 mg/kg) was intravenously injected a total of four times once a day, and tumor growth (volume) was then monitored at predetermined time intervals.
Figure 14B:
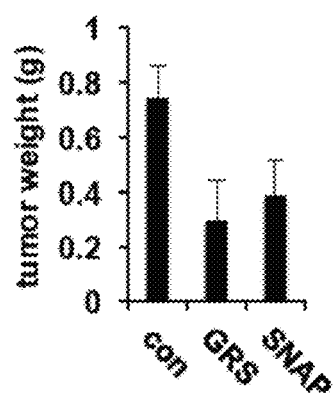
FIG. 14b illustrates the results or tumor weight in tumor xenograft models. The tumor xenograft models were constructed by subcutaneously injecting H460 cells into nude mice, and on day 7 after tumor implantation, ARS-SPs (SNAPs, 6 mg/kg) or GRS (6 mg/kg) was intravenously injected a total of four times once a day, and on the last day of the test, the tumor weight was measured.

The anticancer effect was evaluated in other tumor models constructed by the same method as in example 2 above. H460 cells were first implanted into nude mice, and on day 1 after the implantation, ARS-SPs or GRS was injected once a day for a total of four days. In the above case, ARS-SP and GRS suppressed the growth of all tumors (FIGS. 14a and 14b), and hardly affected the body weight.

Considering that the same amount of the ARS-SP and GRS were also used for in vivo tests, the ARS-SP of the present invention showed a higher cancer cell apoptotic efficacy than GRS proteins.

<11-3> Evaluation on GRS Content Inside ARS-SP

Then, the contribution of GRS, existing in the ARS-SP, to anticancer activity was monitored. The isolated ARS-SPs and naked GRS reduced the viability of H460 cells by 50% and 40%, respectively, when compared with the non-treatment control group (FIG. 15).

Figure 15:
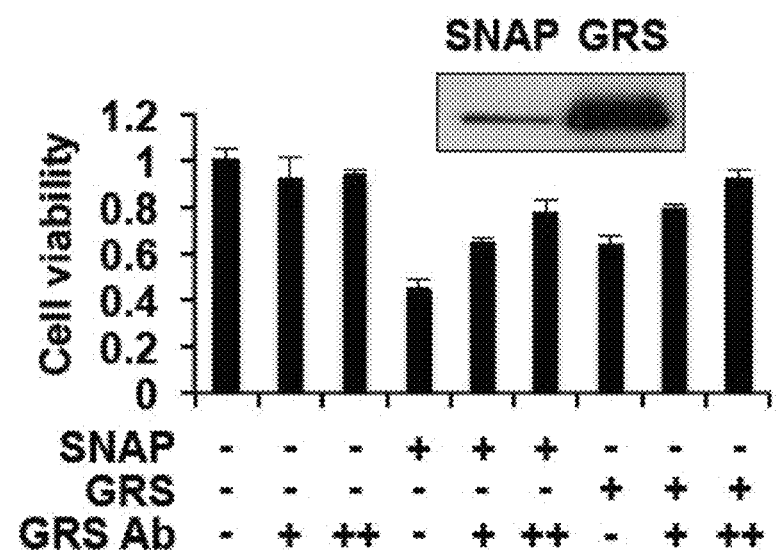
FIG. 15 illustrates the test results of the extent of which GRS present in ARS-SP (SNAP) contributes to ARS-SP (SNAP)'s anticancer activity. Cell viability of cancer cells treated with ARS-SP and GRS was determined by MTT assay. H460 cells were cultured together with ARS-SPs (10 μg/ml) for 24 hr. Purified his-tagged GRS protein (100 nM) was used as a control. In order to neutralize the effect of GRS, ARS-SP or GRS was pre-incubated together with anti-GRS antibody for 30 min, and thereafter, the incubated substance was added to the H460 cell culture medium. The amount of naked GRS used in the present test and the amount of GRS present in ARS-SP were compared by immunoblotting (insert at right upper side).

When the western blotting was used to compare the amount of GRS existing in the ARS-SP with that of the naked GRS, the GRS in the ARS-SP was shown to be 10-fold lower than the naked GRS (insert at right upper side of FIG. 15). However, the ARS-SP exhibited a higher efficacy in the suppression of cancer cells than GRS, suggesting the presence of another factors contributing to the cytotoxicity of cancer cells, in addition to GRS. This fact has been confirmed in Example 7 above.

INDUSTRIAL APPLICABILITY

As described above, the present invention provides: nanoparticles comprising glycyl-tRNA synthetase (GRS), leucyl-tRNA synthetase (LRS), and isoleucyl-tRNA synthetase (IRS) and possessing an activity of treating cancer or enhancing immune function; a pharmaceutical composition for preventing or treating cancer comprising the nanoparticles as an active ingredient; and a method for preparing the nanoparticles. The nanoparticles and the composition comprising the same are effective in preventing or treating cancer, and thus are highly industrially applicable.

The invention claimed is:

1. A method for treating cancer or enhancing immune function in a subject, the method comprising administering an effective amount of nanoparticles to a subject in need of treating cancer or enhancing immune function,
   wherein the nanoparticles comprise glycyl-tRNA synthetase (GRS), leucyl-tRNA synthetase (LRS), and isoleucyl-tRNA synthetase (IRS),
   wherein the GRS comprises an amino acid sequence of SEQ ID NO: 1 and the $390^{th}$ amino acid cysteine in the amino acid sequence of SEQ ID NO: 1 is palmitoylated.

2. The method of claim 1, wherein the cancer is at least one selected from the group consisting of breast cancer, colorectal cancer, lung cancer, small cell lung cancer, gastric cancer, liver cancer, blood cancer, bone cancer, pancreatic cancer, skin cancer, head or neck cancer, cutaneous or intraocular melanoma, eye tumor, peritoneal cancer, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, urethral cancer, penile cancer, prostate cancer, testicular cancer, oral cancer, gallbladder cancer, cholangiocarcinoma, chronic or acute leukemia, lymphocyte lymphoma, bladder cancer, kidney cancer, ureteral cancer, renal cell carcinoma, renal pelvic carcinoma, CNS tumor, primary CNS lymphoma, spinal cord tumor, brain stem glioma, and pituitary adenoma.

3. The method of claim 1, wherein the LRS comprises an amino acid sequence of SEQ ID NO: 2, and the IRS comprises an amino acid sequence of SEQ ID NO: 3.

4. The method of claim 1, wherein the nanoparticles are prepared by a method comprising:
   (a) inducing an artificial apoptotic stress to cells;
   (b) collecting nanoparticles secreted from the cells in step (a); and
   (c) determining whether the collected nanoparticles comprise glycyl-tRNA synthetase (GRS), leucyl-tRNA synthetase (LRS), and isoleucyl-tRNA synthetase (IRS),
   wherein the GRS comprises an amino acid sequence represented by SEQ ID NO: 1 and the $390^{th}$ amino acid cysteine in the amino acid sequence of SEQ ID NO: 1 is palmitoylated.

5. The method of claim 4, wherein the apoptotic stress is at least one selected from the group consisting of oxygen deficiency, glucose starvation, Fas ligand treatment, tumor necrosis factor-α (TNF-α) treatment, TNF-β treatment, TNF-related apoptosis inducing ligand (TRAIL) treatment, perforin treatment, Bax protein treatment, Bak protein treatment, and adriamycin treatment.

6. The method of claim 4, wherein the cells in step (a) are immune cells.

7. The method of claim 1, wherein the nanoparticles are prepared by a method comprising:
   (a) co-culturing non-cancer cells and cancer cells;
   (b) collecting nanoparticles secreted from the non-cancer cells in step (a); and
   (c) determining whether the collected nanoparticles comprise glycyl-tRNA synthetase (GRS), leucyl-tRNA synthetase (LRS), and isoleucyl-tRNA synthetase (IRS),
   wherein the GRS comprises an amino acid sequence represented by SEQ ID NO: 1 and the $390^{th}$ amino acid cysteine in the amino acid sequence of SEQ ID NO: 1 is palmitoylated.

8. The method of claim 7, the method further comprises (d) differentiating exosomes from the nanoparticles collected in step (b).

9. The method of claim 8, wherein the exosomes comprise at least one marker selected from the group consisting of syntenin-1, CD9, CD63, and CD81.

10. The method of claim 7, wherein the nanoparticles further comprise vimentin and insulin-like growth factor 2 receptor (IGF2R).

11. The method of claim 7, wherein the non-cancer cells in step (a) are immune cells.

* * * * *

SEQUENCE LISTING

<160> NUMBER OF SEQ ID NOS: 11

<210> SEQ ID NO 1
<211> LENGTH: 685
<212> TYPE: PRT
<213> ORGANISM: Artificial Sequence
<220> FEATURE:
<223> OTHER INFORMATION: GRS(Glycyl tRNA synthetase)

<400> SEQUENCE: 1

Met Asp Gly Ala Gly Ala Glu Glu Val Leu Ala Pro Leu Arg Leu Ala
 1               5                  10                  15

Val Arg Gln Gln Gly Asp Leu Val Arg Lys Leu Lys Glu Asp Lys Ala
            20                  25                  30

Pro Gln Val Asp Val Asp Lys Ala Val Ala Glu Leu Lys Ala Arg Lys
        35                  40                  45

Arg Val Leu Glu Ala Lys Glu Leu Ala Leu Gln Pro Lys Asp Asp Ile
    50                  55                  60

Val Asp Arg Ala Lys Met Glu Asp Thr Leu Lys Arg Arg Phe Phe Tyr
65                  70                  75                  80

Asp Gln Ala Phe Ala Ile Tyr Gly Gly Val Ser Gly Leu Tyr Asp Phe
                85                  90                  95

Gly Pro Val Gly Cys Ala Leu Lys Asn Asn Ile Ile Gln Thr Trp Arg
            100                 105                 110

Gln His Phe Ile Gln Glu Glu Gln Ile Leu Glu Ile Asp Cys Thr Met
        115                 120                 125

Leu Thr Pro Glu Pro Val Leu Lys Thr Ser Gly His Val Asp Lys Phe
    130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                165                 170                 175

Cys Ser Val Glu Lys Lys Ser Glu Met Glu Ser Val Leu Ala Gln Leu
            180                 185                 190

Asp Asn Tyr Gly Gln Gln Glu Leu Ala Asp Leu Phe Val Asn Tyr Asn
        195                 200                 205

Val Lys Ser Pro Ile Thr Gly Asn Asp Leu Ser Pro Pro Val Ser Phe
    210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
            260                 265                 270

Gly Asn Ser Phe Arg Asn Glu Ile Ser Pro Arg Ser Gly Leu Ile Arg
        275                 280                 285

Val Arg Glu Phe Thr Met Ala Glu Ile Glu His Phe Val Asp Pro Ser
    290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
            340                 345                 350

Gly Tyr Phe Ile Gly Arg Ile Tyr Leu Tyr Leu Thr Lys Val Gly Ile

```
                355                 360                 365
Ser Pro Asp Lys Leu Arg Phe Arg Gln His Met Glu Asn Glu Met Ala
370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
            420                 425                 430

Lys Glu Pro Lys Thr Val Asn Val Gln Phe Glu Pro Ser Lys Gly
        435                 440                 445

Ala Ile Gly Lys Ala Tyr Lys Lys Asp Ala Lys Leu Val Met Glu Tyr
    450                 455                 460

Leu Ala Ile Cys Asp Glu Cys Tyr Ile Thr Glu Met Glu Met Leu Leu
465                 470                 475                 480

Asn Glu Lys Gly Glu Phe Thr Ile Glu Thr Gly Lys Thr Phe Gln
                485                 490                 495

Leu Thr Lys Asp Met Ile Asn Val Lys Arg Phe Gln Lys Thr Leu Tyr
            500                 505                 510

Val Glu Val Val Pro Asn Val Ile Glu Pro Ser Phe Gly Leu Gly
        515                 520                 525

Arg Ile Met Tyr Thr Val Phe Glu His Thr Phe His Val Arg Glu Gly
    530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
            580                 585                 590

Val Asp Asp Ser Ser Gly Ser Ile Gly Arg Arg Tyr Ala Arg Thr Asp
        595                 600                 605

Glu Ile Gly Val Ala Phe Gly Val Thr Ile Asp Phe Asp Thr Val Asn
    610                 615                 620

Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
                645                 650                 655

Asn Gly Asn Ile Thr Trp Ala Asp Val Glu Ala Arg Tyr Pro Leu Phe
            660                 665                 670

Glu Gly Gln Glu Thr Gly Lys Lys Glu Thr Ile Glu Glu
        675                 680                 685

<210> SEQ ID NO 2
<211> LENGTH: 1176
<212> TYPE: PRT
<213> ORGANISM: Artificial Sequence
<220> FEATURE:
<223> OTHER INFORMATION: LRS(Leucyl tRNA synthetase)

<400> SEQUENCE: 2

Met Ala Glu Arg Lys Gly Thr Ala Lys Val Asp Phe Leu Lys Lys Ile
1               5                   10                  15

Glu Lys Glu Ile Gln Gln Lys Trp Asp Thr Glu Arg Val Phe Glu Val
            20                  25                  30

Asn Ala Ser Asn Leu Glu Lys Gln Thr Ser Lys Gly Lys Tyr Phe Val
```

```
             35                  40                  45
Thr Phe Pro Tyr Pro Tyr Met Asn Gly Arg Leu His Leu Gly His Thr
 50                  55                  60

Phe Ser Leu Ser Lys Cys Glu Phe Ala Val Gly Tyr Gln Arg Leu Lys
 65                  70                  75                  80

Gly Lys Cys Cys Leu Phe Pro Phe Gly His Cys Thr Gly Met Pro
                 85                  90                  95

Ile Lys Ala Cys Ala Asp Lys Leu Lys Arg Glu Ile Glu Leu Tyr Gly
                100                 105                 110

Cys Pro Pro Asp Phe Pro Asp Glu Glu Glu Glu Glu Thr Ser
                115                 120                 125

Val Lys Thr Glu Asp Ile Ile Ile Lys Asp Lys Ala Lys Gly Lys Lys
130                 135                 140

Ser Lys Ala Ala Ala Lys Ala Gly Ser Ser Lys Tyr Gln Trp Gly Ile
145                 150                 155                 160

Met Lys Ser Leu Gly Leu Ser Asp Glu Glu Ile Val Lys Phe Ser Glu
                165                 170                 175

Ala Glu His Trp Leu Asp Tyr Phe Pro Pro Leu Ala Ile Gln Asp Leu
                180                 185                 190

Lys Arg Met Gly Leu Lys Val Asp Trp Arg Arg Ser Phe Ile Thr Thr
                195                 200                 205

Asp Val Asn Pro Tyr Tyr Asp Ser Phe Val Arg Trp Gln Phe Leu Thr
                210                 215                 220

Leu Arg Glu Arg Asn Lys Ile Lys Phe Gly Lys Arg Tyr Thr Ile Tyr
225                 230                 235                 240

Ser Pro Lys Asp Gly Gln Pro Cys Met Asp His Asp Arg Gln Thr Gly
                245                 250                 255

Glu Gly Val Gly Pro Gln Glu Tyr Thr Leu Leu Lys Leu Lys Ala Leu
                260                 265                 270

Glu Pro Tyr Pro Ser Lys Leu Ser Gly Leu Lys Gly Lys Asn Ile Phe
                275                 280                 285

Leu Val Ala Ala Thr Leu Arg Pro Glu Thr Met Phe Gly Gln Thr Asn
290                 295                 300

Cys Trp Val Arg Pro Asp Met Lys Tyr Ile Gly Phe Glu Thr Val Asn
305                 310                 315                 320

Gly Asp Ile Phe Ile Cys Thr Gln Lys Ala Ala Arg Asn Met Ser Tyr
                325                 330                 335

Gln Gly Phe Thr Lys Asp Asn Gly Val Val Pro Val Val Lys Glu Leu
                340                 345                 350

Met Gly Glu Glu Ile Leu Gly Ala Ser Leu Ser Ala Pro Leu Thr Ser
                355                 360                 365

Tyr Lys Val Ile Tyr Val Leu Pro Met Leu Thr Ile Lys Glu Asp Lys
                370                 375                 380

Gly Thr Gly Val Val Thr Ser Val Pro Ser Asp Ser Pro Asp Asp Ile
385                 390                 395                 400

Ala Ala Leu Arg Asp Leu Lys Lys Lys Gln Ala Leu Arg Ala Lys Tyr
                405                 410                 415

Gly Ile Arg Asp Asp Met Val Leu Pro Phe Glu Pro Val Pro Val Ile
                420                 425                 430

Glu Ile Pro Gly Phe Gly Asn Leu Ser Ala Val Thr Ile Cys Asp Glu
                435                 440                 445

Leu Lys Ile Gln Ser Gln Asn Asp Arg Glu Lys Leu Ala Glu Ala Lys
                450                 455                 460
```

```
Glu Lys Ile Tyr Leu Lys Gly Phe Tyr Glu Gly Ile Met Leu Val Asp
465                 470                 475                 480

Gly Phe Lys Gly Gln Lys Val Gln Asp Val Lys Lys Thr Ile Gln Lys
                485                 490                 495

Lys Met Ile Asp Ala Gly Asp Ala Leu Ile Tyr Met Glu Pro Glu Lys
            500                 505                 510

Gln Val Met Ser Arg Ser Ser Asp Glu Cys Val Val Ala Leu Cys Asp
        515                 520                 525

Gln Trp Tyr Leu Asp Tyr Gly Glu Glu Asn Trp Lys Lys Gln Thr Ser
    530                 535                 540

Gln Cys Leu Lys Asn Leu Glu Thr Phe Cys Glu Thr Arg Arg Asn
545                 550                 555                 560

Phe Glu Ala Thr Leu Gly Trp Leu Gln Glu His Ala Cys Ser Arg Thr
                565                 570                 575

Tyr Gly Leu Gly Thr His Leu Pro Trp Asp Glu Gln Trp Leu Ile Glu
            580                 585                 590

Ser Leu Ser Asp Ser Thr Ile Tyr Met Ala Phe Tyr Thr Val Ala His
        595                 600                 605

Leu Leu Gln Gly Gly Asn Leu His Gly Gln Ala Glu Ser Pro Leu Gly
    610                 615                 620

Ile Arg Pro Gln Gln Met Thr Lys Glu Val Trp Asp Tyr Val Phe Phe
625                 630                 635                 640

Lys Glu Ala Pro Phe Pro Lys Thr Gln Ile Ala Lys Glu Lys Leu Asp
                645                 650                 655

Gln Leu Lys Gln Glu Phe Glu Phe Trp Tyr Pro Val Asp Leu Arg Val
            660                 665                 670

Ser Gly Lys Asp Leu Val Pro Asn His Leu Ser Tyr Tyr Leu Tyr Asn
        675                 680                 685

His Val Ala Met Trp Pro Glu Gln Ser Asp Lys Trp Pro Thr Ala Val
    690                 695                 700

Arg Ala Asn Gly His Leu Leu Leu Asn Ser Glu Lys Met Ser Lys Ser
705                 710                 715                 720

Thr Gly Asn Phe Leu Thr Leu Thr Gln Ala Ile Asp Lys Phe Ser Ala
                725                 730                 735

Asp Gly Met Arg Leu Ala Leu Ala Asp Ala Gly Asp Thr Val Glu Asp
            740                 745                 750

Ala Asn Phe Val Glu Ala Met Ala Asp Ala Gly Ile Leu Arg Leu Tyr
        755                 760                 765

Thr Trp Val Glu Trp Val Lys Glu Met Val Ala Asn Trp Asp Ser Leu
    770                 775                 780

Arg Ser Gly Pro Ala Ser Thr Phe Asn Asp Arg Val Phe Ala Ser Glu
785                 790                 795                 800

Leu Asn Ala Gly Ile Ile Lys Thr Asp Gln Asn Tyr Glu Lys Met Met
                805                 810                 815

Phe Lys Glu Ala Leu Lys Thr Gly Phe Phe Glu Phe Gln Ala Ala Lys
            820                 825                 830

Asp Lys Tyr Arg Glu Leu Ala Val Glu Gly Met His Arg Glu Leu Val
        835                 840                 845

Phe Arg Phe Ile Glu Val Gln Thr Leu Leu Leu Ala Pro Phe Cys Pro
    850                 855                 860

His Leu Cys Glu His Ile Trp Thr Leu Leu Gly Lys Pro Asp Ser Ile
865                 870                 875                 880
```

Met Asn Ala Ser Trp Pro Val Ala Gly Pro Val Asp Glu Val Leu Ile
                885                 890                 895

His Ser Ser Gln Tyr Leu Met Glu Val Thr His Asp Leu Arg Leu Arg
            900                 905                 910

Leu Lys Asn Tyr Met Met Pro Ala Lys Gly Lys Lys Thr Asp Lys Gln
        915                 920                 925

Pro Leu Gln Lys Pro Ser His Cys Thr Ile Tyr Val Ala Lys Asn Tyr
    930                 935                 940

Pro Pro Trp Gln His Thr Thr Leu Ser Val Leu Arg Lys His Phe Glu
945                 950                 955                 960

Ala Asn Asn Gly Lys Leu Pro Asp Asn Lys Val Ile Ala Ser Glu Leu
                965                 970                 975

Gly Ser Met Pro Glu Leu Lys Lys Tyr Met Lys Lys Val Met Pro Phe
            980                 985                 990

Val Ala Met Ile Lys Glu Asn Leu Glu Lys Met Gly Pro Arg Ile Leu
        995                 1000                1005

Asp Leu Gln Leu Glu Phe Asp Glu Lys Ala Val Leu Met Glu Asn Ile
    1010                1015                1020

Val Tyr Leu Thr Asn Ser Leu Glu Leu Glu His Ile Glu Val Lys Phe
1025                1030                1035                1040

Ala Ser Glu Ala Glu Asp Lys Ile Arg Glu Asp Cys Cys Pro Gly Lys
                1045                1050                1055

Pro Leu Asn Val Phe Arg Ile Glu Pro Gly Val Ser Val Ser Leu Val
            1060                1065                1070

Asn Pro Gln Pro Ser Asn Gly His Phe Ser Thr Lys Ile Glu Ile Lys
        1075                1080                1085

Gln Gly Asp Asn Cys Asp Ser Ile Ile Arg Arg Leu Met Lys Met Asn
    1090                1095                1100

Arg Gly Ile Lys Asp Leu Ser Lys Val Lys Leu Met Arg Phe Asp Asp
1105                1110                1115                1120

Pro Leu Leu Gly Pro Arg Arg Val Pro Val Leu Gly Lys Glu Tyr Thr
                1125                1130                1135

Glu Lys Thr Pro Ile Ser Glu His Ala Val Phe Asn Val Asp Leu Met
            1140                1145                1150

Ser Lys Lys Ile His Leu Thr Glu Asn Gly Ile Arg Val Asp Ile Gly
        1155                1160                1165

Asp Thr Ile Ile Tyr Leu Val His
    1170                1175

<210> SEQ ID NO 3
<211> LENGTH: 1262
<212> TYPE: PRT
<213> ORGANISM: Artificial Sequence
<220> FEATURE:
<223> OTHER INFORMATION: IRS(Isoleucyl tRNA synthetase)

<400> SEQUENCE: 3

Met Leu Gln Gln Val Pro Glu Asn Ile Asn Phe Pro Ala Glu Glu Glu
1               5                   10                  15

Lys Ile Leu Glu Phe Trp Thr Glu Phe Asn Cys Phe Gln Glu Cys Leu
            20                  25                  30

Lys Gln Ser Lys His Lys Pro Lys Phe Thr Phe Tyr Asp Gly Pro Pro
        35                  40                  45

Phe Ala Thr Gly Leu Pro His Tyr Gly His Ile Leu Ala Gly Thr Ile
    50                  55                  60

-continued

```
Lys Asp Ile Val Thr Arg Tyr Ala His Gln Ser Gly Phe His Val Asp
 65                  70                  75                  80

Arg Arg Phe Gly Trp Asp Cys His Gly Leu Pro Val Glu Tyr Glu Ile
                 85                  90                  95

Asp Lys Thr Leu Gly Ile Arg Gly Pro Glu Asp Val Ala Lys Met Gly
            100                 105                 110

Ile Thr Glu Tyr Asn Asn Gln Cys Arg Ala Ile Val Met Arg Tyr Ser
        115                 120                 125

Ala Glu Trp Lys Ser Thr Val Ser Arg Leu Gly Arg Trp Ile Asp Phe
130                 135                 140

Asp Asn Asp Tyr Lys Thr Leu Tyr Pro Gln Phe Met Glu Ser Val Trp
145                 150                 155                 160

Trp Val Phe Lys Gln Leu Tyr Asp Lys Gly Leu Val Tyr Arg Gly Val
                165                 170                 175

Lys Val Met Pro Phe Ser Thr Ala Cys Asn Thr Pro Leu Ser Asn Phe
            180                 185                 190

Glu Ser His Gln Asn Tyr Lys Asp Val Gln Asp Pro Ser Val Phe Val
        195                 200                 205

Thr Phe Pro Leu Glu Glu Asp Glu Thr Val Ser Leu Val Ala Trp Thr
210                 215                 220

Thr Thr Pro Trp Thr Leu Pro Ser Asn Leu Ala Val Cys Val Asn Pro
225                 230                 235                 240

Glu Met Gln Tyr Val Lys Ile Lys Asp Val Ala Arg Gly Arg Leu Leu
                245                 250                 255

Ile Leu Met Glu Ala Arg Leu Ser Ala Leu Tyr Lys Leu Glu Ser Asp
            260                 265                 270

Tyr Glu Ile Leu Glu Arg Phe Pro Gly Ala Tyr Leu Lys Gly Lys Lys
        275                 280                 285

Tyr Arg Pro Leu Phe Asp Tyr Phe Leu Lys Cys Lys Glu Asn Gly Ala
290                 295                 300

Phe Thr Val Leu Val Asp Asn Tyr Val Lys Glu Glu Gly Thr Gly
305                 310                 315                 320

Val Val His Gln Ala Pro Tyr Phe Gly Ala Glu Asp Tyr Arg Val Cys
                325                 330                 335

Met Asp Phe Asn Ile Ile Arg Lys Asp Ser Leu Pro Val Cys Pro Val
            340                 345                 350

Asp Ala Ser Gly Cys Phe Thr Thr Glu Val Thr Asp Phe Ala Gly Gln
        355                 360                 365

Tyr Val Lys Asp Ala Asp Lys Ser Ile Ile Arg Thr Leu Lys Glu Gln
370                 375                 380

Gly Arg Leu Leu Val Ala Thr Thr Phe Thr His Ser Tyr Pro Phe Cys
385                 390                 395                 400

Trp Arg Ser Asp Thr Pro Leu Ile Tyr Lys Ala Val Pro Ser Trp Phe
                405                 410                 415

Val Arg Val Glu Asn Met Val Asp Gln Leu Leu Arg Asn Asn Asp Leu
            420                 425                 430

Cys Tyr Trp Val Pro Glu Leu Val Arg Glu Lys Arg Phe Gly Asn Trp
        435                 440                 445

Leu Lys Asp Ala Arg Asp Trp Thr Ile Ser Arg Asn Arg Tyr Trp Gly
450                 455                 460

Thr Pro Ile Pro Leu Trp Val Ser Asp Asp Phe Glu Glu Val Val Cys
465                 470                 475                 480

Ile Gly Ser Val Ala Glu Leu Glu Glu Leu Ser Gly Ala Lys Ile Ser
```

```
            485                 490                 495
Asp Leu His Arg Glu Ser Val Asp His Leu Thr Ile Pro Ser Arg Cys
            500                 505                 510

Gly Lys Gly Ser Leu His Arg Ile Ser Glu Val Phe Asp Cys Trp Phe
            515                 520                 525

Glu Ser Gly Ser Met Pro Tyr Ala Gln Val His Tyr Pro Phe Glu Asn
            530                 535                 540

Lys Arg Glu Phe Glu Asp Ala Phe Pro Ala Asp Phe Ile Ala Glu Gly
545                 550                 555                 560

Ile Asp Gln Thr Arg Gly Trp Phe Tyr Thr Leu Leu Val Leu Ala Thr
            565                 570                 575

Ala Leu Phe Gly Gln Pro Pro Phe Lys Asn Val Ile Val Asn Gly Leu
            580                 585                 590

Val Leu Ala Ser Asp Gly Gln Lys Met Ser Lys Arg Lys Lys Asn Tyr
            595                 600                 605

Pro Asp Pro Val Ser Ile Ile Gln Lys Tyr Gly Ala Asp Ala Leu Arg
            610                 615                 620

Leu Tyr Leu Ile Asn Ser Pro Val Val Arg Ala Glu Asn Leu Arg Phe
625                 630                 635                 640

Lys Glu Glu Gly Val Arg Asp Val Leu Lys Asp Val Leu Leu Pro Trp
            645                 650                 655

Tyr Asn Ala Tyr Arg Phe Leu Ile Gln Asn Val Leu Arg Leu Gln Lys
            660                 665                 670

Glu Glu Glu Ile Glu Phe Leu Tyr Asn Glu Asn Thr Val Arg Glu Ser
            675                 680                 685

Pro Asn Ile Thr Asp Arg Trp Ile Leu Ser Phe Met Gln Ser Leu Ile
            690                 695                 700

Gly Phe Phe Glu Thr Glu Met Ala Ala Tyr Arg Leu Tyr Thr Val Val
705                 710                 715                 720

Pro Arg Leu Val Lys Phe Val Asp Ile Leu Thr Asn Trp Tyr Val Arg
            725                 730                 735

Met Asn Arg Arg Arg Leu Lys Gly Glu Asn Gly Met Glu Asp Cys Val
            740                 745                 750

Met Ala Leu Glu Thr Leu Phe Ser Val Leu Leu Ser Leu Cys Arg Leu
            755                 760                 765

Ile Ala Pro Tyr Thr Pro Phe Leu Thr Glu Leu Met Tyr Gln Asn Leu
            770                 775                 780

Lys Val Leu Ile Asp Pro Val Ser Val Gln Asp Lys Asp Thr Leu Ser
785                 790                 795                 800

Ile His Tyr Leu Met Leu Pro Arg Val Arg Glu Leu Ile Asp Lys
            805                 810                 815

Lys Thr Glu Ser Ala Val Ser Gln Met Gln Ser Val Ile Glu Leu Gly
            820                 825                 830

Arg Val Ile Arg Asp Arg Lys Thr Ile Pro Ile Lys Tyr Pro Leu Lys
            835                 840                 845

Glu Ile Val Val Ile His Gln Asp Pro Glu Ala Leu Lys Asp Ile Lys
            850                 855                 860

Ser Leu Glu Lys Tyr Ile Ile Glu Glu Leu Asn Val Arg Lys Val Thr
865                 870                 875                 880

Leu Ser Thr Asp Lys Asn Lys Tyr Gly Ile Arg Leu Arg Ala Glu Pro
            885                 890                 895

Asp His Met Val Leu Gly Lys Arg Leu Lys Gly Ala Phe Lys Ala Val
            900                 905                 910
```

```
Met Thr Ser Ile Lys Gln Leu Ser Ser Glu Glu Leu Glu Gln Phe Gln
        915                 920                 925
Lys Thr Gly Thr Ile Val Val Glu Gly His Glu Leu His Asp Glu Asp
        930                 935                 940
Ile Arg Leu Met Tyr Thr Phe Asp Gln Ala Thr Gly Gly Thr Ala Gln
945                 950                 955                 960
Phe Glu Ala His Ser Asp Ala Gln Ala Leu Val Leu Leu Asp Val Thr
                965                 970                 975
Pro Asp Gln Ser Met Val Asp Glu Gly Met Ala Arg Glu Val Ile Asn
            980                 985                 990
Arg Ile Gln Lys Leu Arg Lys Lys Cys Asn Leu Val Pro Thr Asp Glu
        995                 1000                1005
Ile Thr Val Tyr Tyr Lys Ala Lys Ser Glu Gly Thr Tyr Leu Asn Ser
    1010                1015                1020
Val Ile Glu Ser His Thr Glu Phe Ile Phe Thr Thr Ile Lys Ala Pro
1025                1030                1035                1040
Leu Lys Pro Tyr Pro Val Ser Pro Ser Asp Lys Val Leu Ile Gln Glu
                1045                1050                1055
Lys Thr Gln Leu Lys Gly Ser Glu Leu Glu Ile Thr Leu Thr Arg Gly
            1060                1065                1070
Ser Ser Leu Pro Gly Pro Ala Cys Ala Tyr Val Asn Leu Asn Ile Cys
        1075                1080                1085
Ala Asn Gly Ser Glu Gln Gly Gly Val Leu Leu Leu Glu Asn Pro Lys
    1090                1095                1100
Gly Asp Asn Arg Leu Asp Leu Leu Lys Leu Lys Ser Val Val Thr Ser
1105                1110                1115                1120
Ile Phe Gly Val Lys Asn Thr Glu Leu Ala Val Phe His Asp Glu Thr
                1125                1130                1135
Glu Ile Gln Asn Gln Thr Asp Leu Leu Ser Leu Ser Gly Lys Thr Leu
            1140                1145                1150
Cys Val Thr Ala Gly Ser Ala Pro Ser Leu Ile Asn Ser Ser Ser Thr
        1155                1160                1165
Leu Leu Cys Gln Tyr Ile Asn Leu Gln Leu Leu Asn Ala Lys Pro Gln
    1170                1175                1180
Glu Cys Leu Met Gly Thr Val Gly Thr Leu Leu Leu Glu Asn Pro Leu
1185                1190                1195                1200
Gly Gln Asn Gly Leu Thr His Gln Gly Leu Leu Tyr Glu Ala Ala Lys
                1205                1210                1215
Val Phe Gly Leu Arg Ser Arg Lys Leu Lys Leu Phe Leu Asn Glu Thr
            1220                1225                1230
Gln Thr Gln Glu Ile Thr Glu Asp Ile Pro Val Lys Thr Leu Asn Met
        1235                1240                1245
Lys Thr Val Tyr Val Ser Val Leu Pro Thr Thr Ala Asp Phe
    1250                1255                1260

<210> SEQ ID NO 4
<211> LENGTH: 21
<212> TYPE: DNA
<213> ORGANISM: Artificial Sequence
<220> FEATURE:
<223> OTHER INFORMATION: Forward primer for iNOS

<400> SEQUENCE: 4
cagctgggct gtacaaacct t                                      21
```

```
<210> SEQ ID NO 5
<211> LENGTH: 21
<212> TYPE: DNA
<213> ORGANISM: Artificial Sequence
<220> FEATURE:
<223> OTHER INFORMATION: Reverse primer for iNOS

<400> SEQUENCE: 5
cattggaagt gaagcgtttc g                                              21

<210> SEQ ID NO 6
<211> LENGTH: 20
<212> TYPE: DNA
<213> ORGANISM: Artificial Sequence
<220> FEATURE:
<223> OTHER INFORMATION: Forward primer for Arginase II

<400> SEQUENCE: 6
aagaaaaggc cgattcacct                                                20

<210> SEQ ID NO 7
<211> LENGTH: 20
<212> TYPE: DNA
<213> ORGANISM: Artificial Sequence
<220> FEATURE:
<223> OTHER INFORMATION: Reverse primer for Arginase II

<400> SEQUENCE: 7
cacctcctct gctgtcttcc                                                20

<210> SEQ ID NO 8
<211> LENGTH: 24
<212> TYPE: DNA
<213> ORGANISM: Artificial Sequence
<220> FEATURE:
<223> OTHER INFORMATION: Forward primer for TNF-alpha

<400> SEQUENCE: 8
ctcaaaattc gagtgacaag cctg                                           24

<210> SEQ ID NO 9
<211> LENGTH: 20
<212> TYPE: DNA
<213> ORGANISM: Artificial Sequence
<220> FEATURE:
<223> OTHER INFORMATION: Reverse primer for TNF-alpha

<400> SEQUENCE: 9
atcggctggc accactagtt                                                20

<210> SEQ ID NO 10
<211> LENGTH: 22
<212> TYPE: DNA
<213> ORGANISM: Artificial Sequence
<220> FEATURE:
<223> OTHER INFORMATION: Forward primer for IL-10

<400> SEQUENCE: 10
agactttctt tcaaacaaag ga                                             22

<210> SEQ ID NO 11
<211> LENGTH: 19
<212> TYPE: DNA
<213> ORGANISM: Artificial Sequence
<220> FEATURE:
<223> OTHER INFORMATION: Reverse primer for IL-10
```

```
<400> SEQUENCE: 11
atcgatgaca gcgcctcag                                                    19
```